(12) United States Patent
Nguyen et al.

(10) Patent No.: US 9,822,206 B2
(45) Date of Patent: Nov. 21, 2017

(54) COPOLYMERS FOR NEAR-INFRARED RADIATION-SENSITIVE COATING COMPOSITIONS FOR POSITIVE-WORKING THERMAL LITHOGRAPHIC PRINTING PLATES

(75) Inventors: My T. Nguyen, Ho Chi Minh (VN); Akha Phan, Travinh (VN); Viet-Thu Nguyen-Truong, Travinh (VN); Marc-André Locas, Pierrefonds (CA)

(73) Assignee: MYLAN GROUP, Travinh (VN)

( * ) Notice: Subject to any disclaimer, the term of this patent is extended or adjusted under 35 U.S.C. 154(b) by 1028 days.

(21) Appl. No.: 13/822,976

(22) PCT Filed: Sep. 14, 2010

(86) PCT No.: PCT/CA2010/001401
§ 371 (c)(1),
(2), (4) Date: Mar. 14, 2014

(87) PCT Pub. No.: WO2011/006265
PCT Pub. Date: Jan. 20, 2011

(65) Prior Publication Data
US 2014/0221591 A1    Aug. 7, 2014

(51) Int. Cl.
| | | |
|---|---|---|
| *C08F 220/36* | (2006.01) |
| *C08F 220/60* | (2006.01) |
| *C08F 226/06* | (2006.01) |
| *C08F 212/10* | (2006.01) |
| *C08F 220/50* | (2006.01) |
| *B41C 1/10* | (2006.01) |
| *C07C 233/84* | (2006.01) |
| *C07C 255/19* | (2006.01) |
| *C07C 275/34* | (2006.01) |
| *C07C 275/42* | (2006.01) |
| *C07C 311/46* | (2006.01) |
| *C07D 207/40* | (2006.01) |
| *C07D 209/86* | (2006.01) |
| *C07D 233/74* | (2006.01) |
| *C07D 295/215* | (2006.01) |

(Continued)

(52) U.S. Cl.
CPC .......... *C08F 226/06* (2013.01); *B41C 1/1008* (2013.01); *C07C 233/84* (2013.01); *C07C 255/19* (2013.01); *C07C 275/34* (2013.01); *C07C 275/42* (2013.01); *C07C 311/46* (2013.01); *C07D 207/40* (2013.01); *C07D 209/86* (2013.01); *C07D 233/74* (2013.01); *C07D 295/215* (2013.01); *C08F 2/46* (2013.01); *C08F 12/22* (2013.01); *C08F 12/24* (2013.01); *C08F 12/26* (2013.01); *C08F 12/30* (2013.01); *C08F 212/10* (2013.01); *C08F 212/14* (2013.01); *C08F 220/06* (2013.01); *C08F 220/14* (2013.01); *C08F 220/50* (2013.01); *C09D 125/18* (2013.01); *G03F 7/004* (2013.01); *B41C 2210/02* (2013.01); *B41C 2210/08* (2013.01); *B41C 2210/22* (2013.01); *B41C 2210/24* (2013.01); *C08F 220/36* (2013.01); *C08F 2220/343* (2013.01); *C08F 2220/346* (2013.01); *C08F 2220/387* (2013.01); *C08F 2220/603* (2013.01); *C08F 2220/606* (2013.01)

(58) Field of Classification Search
CPC ................ C08F 212/10; C08F 220/343; C08F 220/346; C08F 220/387; C08F 220/603; C08F 220/606; C08F 220/42; C08F 220/50; C08F 20/50; C08F 226/06
See application file for complete search history.

(56) References Cited

U.S. PATENT DOCUMENTS

| | | |
|---|---|---|
| 2,839,511 A | 6/1958 | Harris et al. |
| 3,933,715 A | 1/1976 | Botsch et al. |

(Continued)

FOREIGN PATENT DOCUMENTS

| | | |
|---|---|---|
| CN | 101479663 A | 6/2009 |
| EP | 0083971 A2 | 7/1983 |

(Continued)

OTHER PUBLICATIONS

Australian Patent Examination Report for Application No. 2010273146, dated Jan. 9, 2014. 5 pages.
Nair et al. 'Cyanate Ester Resins, Recent Developments'. New Polymerization Techniques and Synthetic Methodologies. 2001, vol. 155 pp. 1-99.
CAS Registry No. 346587-51-7, American Chemical Company, 2014, 1 page.
European Supplementary Search Report as it relates to PCT/CA2010001400, dated Mar. 18, 2015.
U.S. Appl. No. 13/391,363, filed Feb. 20, 2012, My T. Nguyen.
Urankar, et al.; Photogenerated Base in Polymer Curing and Imaging: Cross-Linking of Base-Sensitive Polymers Containing Enolizable Pendant Groups; Cehm. Mater.; 1997; 9: 2861-2868.

(Continued)

*Primary Examiner* — Ling Choi
*Assistant Examiner* — David L Miller
(74) *Attorney, Agent, or Firm* — Lathrop Gage LLP; Brian C. Trinque

(57) ABSTRACT

There is provided a copolymer having the general structure below, wherein a, b, and d are molar ratios varying between about 0.01 and about 0.90 and c is a molar ratio varying between about 0.01 and about 0.90; A1 represents monomer units comprising a cyano-containing pendant group in which the cyano is not directly attached to the backbone of the copolymer; A2 represents monomer units comprising two or more hydrogen bonding sites; A3 represents monomer units that increase solubility in organic solvents; and A4 represents monomer units that increase solubility in aqueous alkaline solutions. There is also provided a near-infrared radiation-sensitive coating composition comprising this copolymer as well as a positive-working thermal lithographic printing plate comprising a near-infrared radiation-sensitive coating comprising this copolymer, a method of producing such a printing plate, and finally a method of printing using such a printing plate. Formula (I).

21 Claims, No Drawings

(51) Int. Cl.
- *C08F 12/22* (2006.01)
- *C08F 12/24* (2006.01)
- *C08F 12/26* (2006.01)
- *C08F 12/30* (2006.01)
- *C08F 212/14* (2006.01)
- *C08F 220/06* (2006.01)
- *C08F 220/14* (2006.01)
- *C09D 125/18* (2006.01)
- *G03F 7/004* (2006.01)
- *C08F 2/46* (2006.01)
- *C08F 220/38* (2006.01)
- *C08F 220/34* (2006.01)

(56) References Cited

U.S. PATENT DOCUMENTS

| | | |
|---|---|---|
| 4,297,431 A | 10/1981 | Sullivan |
| 4,345,017 A | 8/1982 | Cournoyer et al. |
| 5,397,690 A | 3/1995 | Fabricius et al. |
| 5,569,573 A | 10/1996 | Takahashi et al. |
| 5,807,932 A | 9/1998 | Pfaendner et al. |
| 5,955,539 A | 9/1999 | Nishikawa |
| 6,107,488 A | 8/2000 | Bouchet et al. |
| 6,124,425 A | 9/2000 | Nguyen |
| 6,132,929 A | 10/2000 | Nakamura et al. |
| 6,177,182 B1 | 1/2001 | Nguyen |
| 6,261,740 B1 | 7/2001 | Nguyen et al. |
| 6,326,122 B1 | 12/2001 | Nagasaka et al. |
| 6,355,396 B1 | 3/2002 | Nakamura |
| 6,410,203 B1 | 6/2002 | Nakamura |
| 6,582,882 B2 | 6/2003 | Pappas et al. |
| 6,805,052 B2 | 10/2004 | Aert et al. |
| 6,846,614 B2 | 1/2005 | Timpe et al. |
| 6,884,568 B2 | 4/2005 | Timpe et al. |
| 6,899,994 B2 | 5/2005 | Huang et al. |
| 6,960,422 B2 | 11/2005 | Goto |
| 6,969,575 B2 | 11/2005 | Inno |
| 6,983,694 B2 | 1/2006 | Vermeersch et al. |
| 7,001,704 B2 | 2/2006 | Oshima et al. |
| 7,060,415 B2 | 6/2006 | Kitson et al. |
| 7,060,416 B2 | 6/2006 | Ray et al. |
| 7,258,961 B2 | 8/2007 | Oda et al. |
| 7,261,998 B2 | 8/2007 | Hayashi et al. |
| 7,371,504 B2 | 5/2008 | Nakamura |
| 7,473,515 B2 | 1/2009 | Nguyen et al. |
| 8,084,564 B2 | 12/2011 | Kano et al. |
| 2002/0160299 A1 | 10/2002 | Asawa et al. |
| 2005/0123853 A1 | 6/2005 | Munnelly et al. |
| 2007/0134590 A1 | 6/2007 | Fukuhara et al. |
| 2007/0269739 A1 | 11/2007 | Nguyen et al. |
| 2008/0139737 A1* | 6/2008 | Alderfer ............... C08L 33/14 524/521 |
| 2008/0171286 A1 | 7/2008 | Nguyen et al. |
| 2009/0035694 A1 | 2/2009 | Nguyen et al. |
| 2009/0042135 A1* | 2/2009 | Patel ............... B41C 1/1016 430/287.1 |
| 2009/0111051 A1 | 4/2009 | Tao et al. |
| 2009/0186299 A1 | 7/2009 | Tao et al. |
| 2010/0021844 A1 | 1/2010 | Yu et al. |
| 2012/0190810 A1 | 7/2012 | Nguyen et al. |

FOREIGN PATENT DOCUMENTS

| | | | |
|---|---|---|---|
| EP | 0550998 A1 | | 12/1992 |
| EP | 1 136 886 A1 | | 9/2001 |
| EP | 1136886 A1 | | 9/2001 |
| EP | 0 770 495 B1 | | 6/2002 |
| EP | 1429184 A1 | | 6/2004 |
| EP | 1437232 B1 | | 1/2007 |
| GB | 780284 | | 7/1957 |
| JP | 62063595 | | 3/1987 |
| JP | 10287823 A | | 10/1998 |
| JP | 11119427 A | * | 4/1999 |
| JP | 11119427 A | | 4/1999 |
| JP | 2008503365 A | | 2/2008 |
| JP | 2008/083159 A | | 4/2008 |
| JP | 2008/299350 A | | 12/2008 |
| JP | 2009046624 A | | 3/2009 |
| JP | 2009191107 A | | 8/2009 |
| JP | 2010/002762 A | | 1/2010 |
| KR | 10-2009-0073079 A | | 7/2009 |
| WO | 2008048749 A2 | | 4/2008 |
| WO | 2011050442 A1 | | 5/2011 |

OTHER PUBLICATIONS

Reghunadhan, et al.; Advances in Polymer Science; 2001; ISBN 3-540-41435-5; Springer-Verlag Berlin heidelberg New York; Library of Congress Catalog Card No. 61642; (2001); p. 64 (3 pages).

Chiang, et al.; Copolymerization of N-(4-Carboxyphenyl)-maleimide with Acrylonitrile and the Properties of Its Membrane; J. Polymer Research; (2000) vol. 7, No. 4; pp. 251-255.

Zhang, et al.; The Electropolymerization of Poly(styrene-co-4-carbosyphenyl maleimide) Coatings onto Steel; J. Applied Polymer Sci.; (1996); vol. 62; pp. 1303-1312.

Mitsuishi, et al.; Mechanical Properties of Polypropylene Filled with Calcium Carbonate; Polymer Engineering and Science; (1985); vol. 25; No. 17; pp. 1069-1073.

CAS No. 6976-93-8, American Chemical Society, 2012, 3 pages.

CAS No. 923-26-2, American Chemical Society, 2012, 3 pages.

CAS No. 868-77-9, American Chemical Society, 2012, 6 pages.

Sun, et al.; Durable and Refreshable Polymeric N-Halamine Biocides Containing 3-(4'-vinylbenzyl)-5,5-dimethylhydantoin; J. Polymer Sci; (2001); vol. 30, pp. 3348-3355.

CAS No. 100-42-5, American Chemical Society, 2012, 10 pages.

CAS No. 1484-13.5, American Chemical Society, 2012, 4 pages.

International Search Report and Written Opinion, PCT/CA2010/001400, dated Dec. 15, 2010, 12 pages.

International Search Report and Written Opinion, PCT/CA2010/001401, dated Jun. 2, 2011, 12 pages.

* cited by examiner

COPOLYMERS FOR NEAR-INFRARED RADIATION-SENSITIVE COATING COMPOSITIONS FOR POSITIVE-WORKING THERMAL LITHOGRAPHIC PRINTING PLATES

RELATED APPLICATIONS

The present application claims the benefit of priority of International Application No. PCT/CA2010/001401 filed Sep. 14, 2010. The entire contents of each of the above documents are incorporated herein by reference.

FIELD OF THE INVENTION

The present invention relates to thermal lithographic printing plates and their coatings. More specifically, the invention relates to copolymers for use in near-infrared radiation-sensitive coating compositions for positive-working thermal lithographic printing plates.

BACKGROUND OF THE INVENTION

In lithographic printing, a printing plate is mounted on the cylinder of a printing press. The printing plate carries a lithographic image on its surface and a printed copy is obtained by applying ink to the image and then transferring the ink from the printing plate onto a receiver material, which typically is a sheet of paper. Generally, the ink is first transferred to an intermediate blanket, which in turn transfers the ink to the surface of the receiver material (offset printing).

In conventional, so-called "wet" lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. When the surface of the printing plate is moistened with water and ink is applied, the hydrophilic regions retain water and repel ink, and the ink-receptive regions accept ink and repel water. During printing, the ink is transferred to the surface of the receiver material upon which the image is to be reproduced.

Lithographic printing plates typically comprise an imageable layer (also called imaging layer or coating) applied over the hydrophilic surface of a substrate, typically aluminium. The imageable layer includes one or more radiation-sensitive components, often dispersed in a suitable binder.

To produce the lithographic image on the printing plate, the printing plate is imaged by targeted radiation. This can be carried out in different ways. In direct digital imaging (computer-to-plate), printing plates can be imaged with infrared or UV lasers or light sources. Such a laser beam can be digitally controlled via a computer; i.e. the laser can be turned on or off so that imagewise exposure of the precursor can be affected via stored digitized information in the computer. Therefore, the imageable layers of printing plates, which are to be imagewise exposed by means of such image-setters, need to be sensitive to radiation in the near-infrared (NIR) or ultraviolet (UV) regions of the spectrum. Thermal lithographic plates are plates sensitive to near-infrared radiation.

The imaging device will etch the image on the printing plate by eliciting a localized transformation of the imageable layer. Indeed, in such imaged systems, the imageable layer typically contains a dye or pigment that absorbs the incident radiation and the absorbed energy initiates the reaction producing the image. Exposure to radiation triggers a physical or chemical process in the imageable layer so that the imaged areas become different from the non-imaged areas and development will produce an image on the printing plate. The change in the imageable layer can be a change of hydrophilicity/oleophilicity, solubility, hardness, etc.

Following exposure, either the exposed regions or the unexposed regions of the imageable layer are removed by a suitable developer, revealing the underlying hydrophilic surface of the substrate. Developers are typically aqueous alkaline solutions, which can contain inorganic salts, such as sodium metasilicate, sodium hydroxide or potassium hydroxide and surfactants.

Alternatively, "on-press developable" lithographic printing plate can be directly mounted on a press after imaging, and are developed through contact with ink and/or fountain solution during initial press operation. In other words, either the exposed regions or the unexposed regions of the imageable layer are removed by the ink and/or fountain solution, not by a developer. More specifically, a so-called on-press development system is one in which an exposed printing plate is fixed on the plate cylinder of a printing press, and a fountain solution and ink are fed thereto while revolving the cylinder to remove non-image areas. This technique allows an imaged, but un-developed printing plate (also called a printing plate precursor) to be mounted as is on a press and be made into a printing plate on an ordinary printing line.

If the exposed regions are removed, the precursor is positive working. Conversely, if the unexposed regions are removed, the precursor is negative working. In each instance, the regions of the imageable layer (i.e., the image areas) that remain are ink-receptive, and the regions of the hydrophilic surface revealed by the developing process accept water and aqueous solutions, typically a fountain solution, and do not accept ink.

The use of copolymers comprising a cyano (—CN) group directly attached to the polymeric backbone for manufacturing single- and multiple-layer positive-working thermal lithographic offset printing plates is known in the art. These copolymers with cyano (—CN) groups directly attached to the polymeric backbone typically provide good film-forming properties, mechanical strength and chemical resistance on press.

Acrylonitrile and methacrylonitrile are liquids with low boiling point (<100° C.). They have recently been classified as hazardous and very toxic materials. They thus require special handling and permission for transportation. Acrylonitrile and methacrylonitrile residues cannot be released from a product in excess of 1 ppm (airborne concentration) as an eight (8)-hour time-weighted average, under the expected conditions of processing, use, and handling. Such requirement is very difficult to achieve when using acrylonitrile and methacrylonitrile containing copolymers for the production of lithographic offset printing plates.

SUMMARY OF THE INVENTION

In accordance with the present invention, there is provided:
1. A copolymer having the general structure:

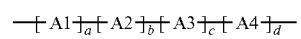

wherein
a, b, and d are molar ratios varying between about 0.01 and about 0.90 and c is a molar ratio varying between 0 and about 0.90,
A1 represents monomer units comprising a cyano-containing pendant group in which the cyano is not directly attached to the backbone of the copolymer;

A2 represents monomer units comprising two or more hydrogen bonding sites;
A3 represents monomer units that increase solubility in organic solvents; and
A4 represents monomer units that increase solubility in aqueous alkaline solutions.

2. The copolymer of item 1, wherein A1 is of formula:

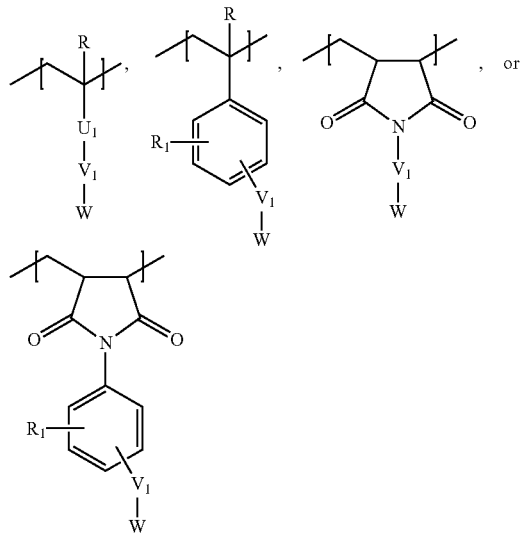

wherein:
R is hydrogen, methyl or ethyl,
R$_1$ is absent or represents one to four alkyl substituents; the alkyl substituents optionally comprising one or more ether, ester, amine, amide, urea, piperazinyl, sulfonamide, or carbamate functional groups, the alkyl substituents optionally being substituted with one or more cyano,
U$_1$ is an amide or ester linker,
V$_1$ is absent or represents alkyl optionally comprising one or more ether, ester, amine, amide, urea, piperazinyl, sulfonamide or carbamate functional group, the alkyl optionally being substituted with one or more cyano, and
W is —CN or

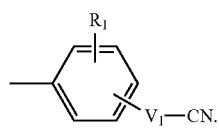

3. The copolymer of item 1 or 2, wherein A1 is

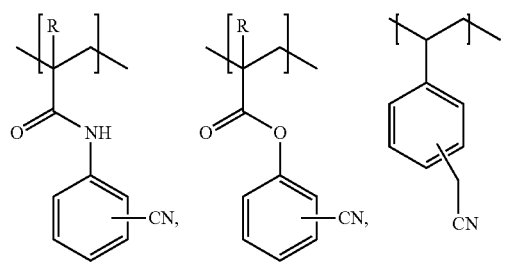

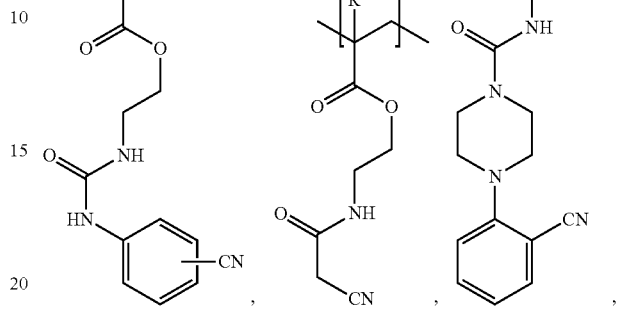

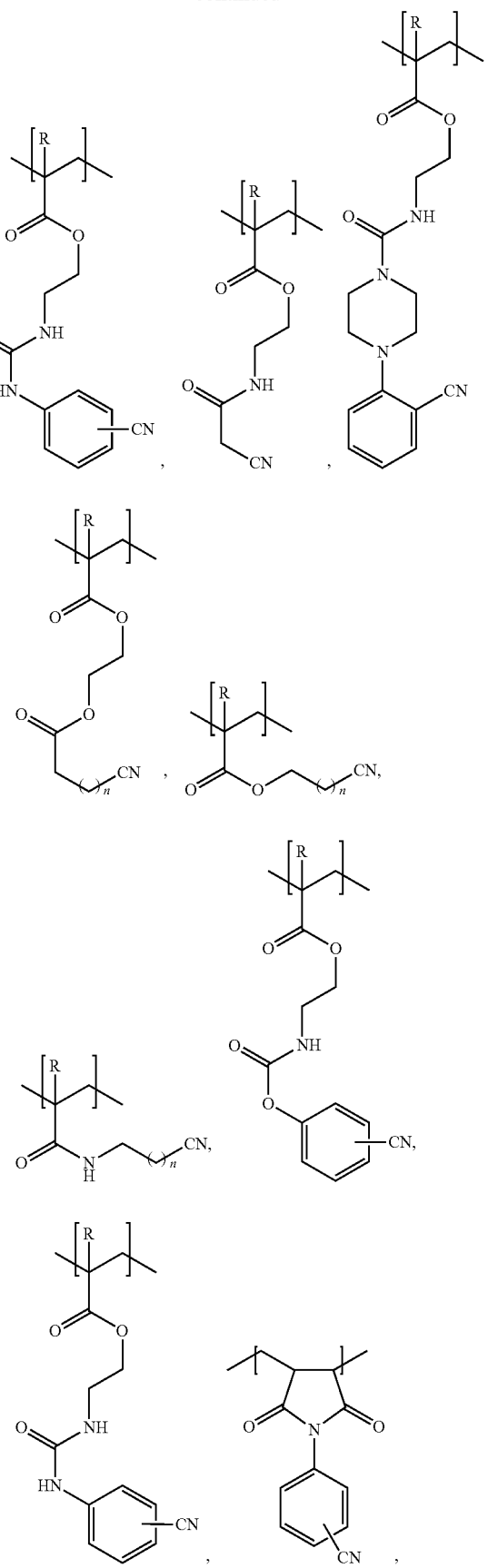

-continued

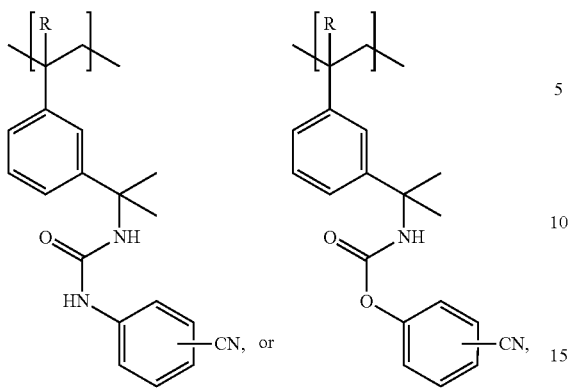

wherein R is hydrogen, methyl or ethyl and n varies between 1 and 10.

4. The copolymer of any one of items 1 to 3, wherein A2 comprises a pendant group comprising a 5,5-dialkylhydantoin group such as a 5,5-dimethylhydantoin group, an aminosulfonamide group, or hydroxy group.

5. The copolymer of any one of items 1 to 3, wherein A2 is of formula:

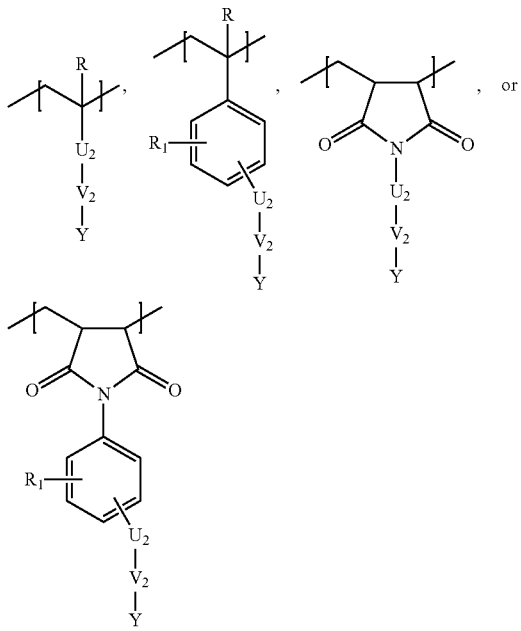

wherein:

R is hydrogen, methyl or ethyl, $R_1$ is absent or represents one to four alkyl substituents, the alkyl substituents optionally comprising one or more ether, ester, amine, amide, urea, piperazinyl, sulfonamide, or carbamate functional groups, $U_2$ is absent or represents an amide or ester linker, $V_2$ is absent or represents alkyl optionally comprising one or more ether, ester, amine, amide, urea, piperazinyl, sulfonamide or carbamate functional group, and Y is —OH, —SO$_2$—NH—R$_2$,

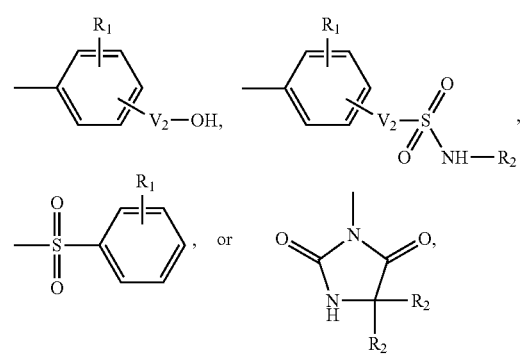

wherein $R_2$ each time it appears is independently hydrogen or alkyl optionally comprising one or more ether, ester, amine, amide, urea, piperazinyl, sulfonamide, or carbamate functional group.

6. The copolymer of item 5, wherein Y is

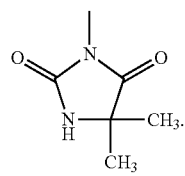

7. The copolymer of item 5, wherein A2 is:

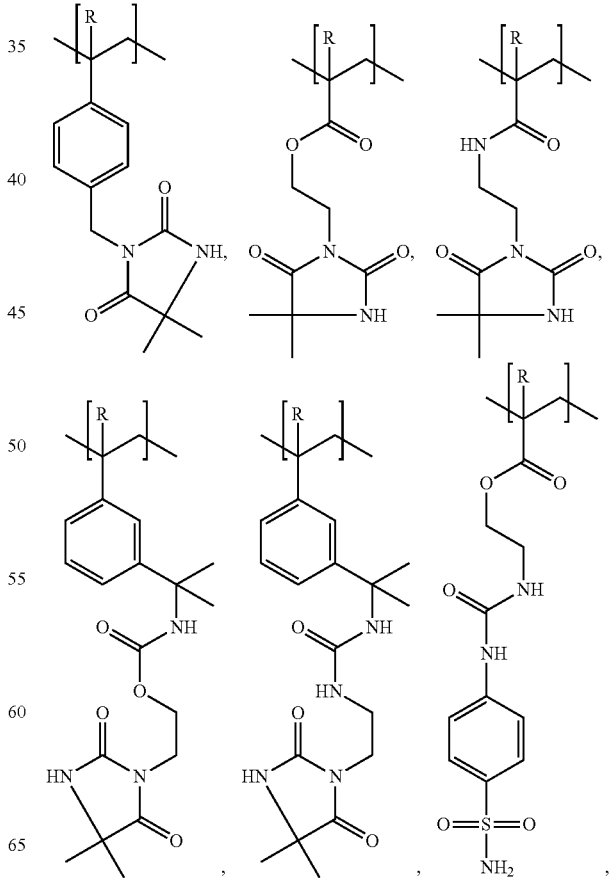

-continued

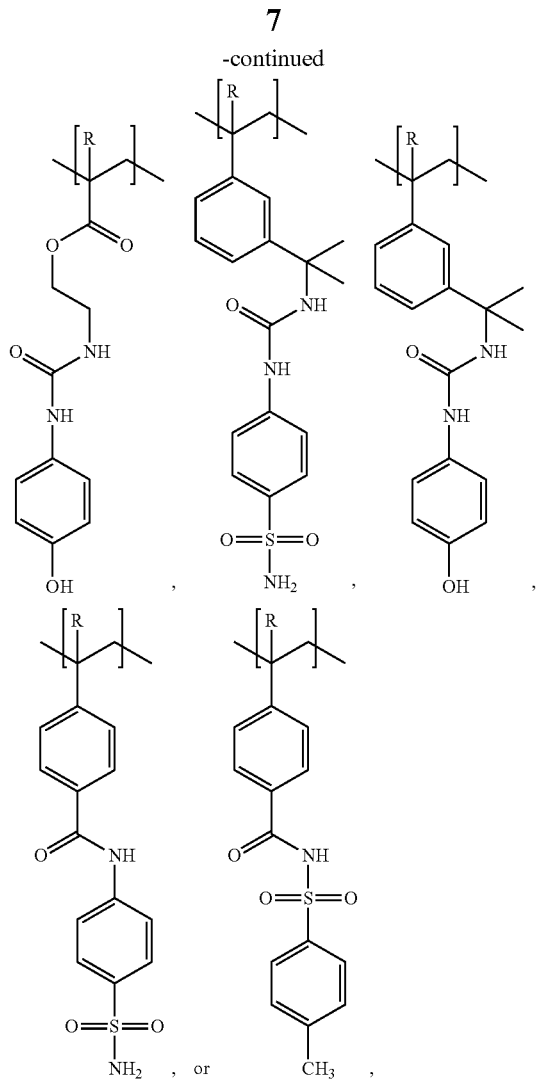

8. The copolymer of any one of items 1 to 7, wherein c varies between about 0.01 and about 0.90.
9. The copolymer of item 8, wherein A3 comprises an alkyl or aryl pendant group, the aryl being eventually substituted with alkyl.
10. The copolymer of item 8, wherein A3 is of formula:

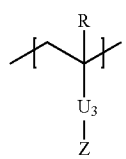

wherein
R is hydrogen, methyl or ethyl,
U$_3$ is absent and is an amide or ester linker, and
Z is alkyl or aryl, the alkyl being optionally substituted with one or more hydroxy, alkyloxy or halide and the aryl being optionally substituted with one or more alkyls that are optionally substituted with one or more hydroxy, alkyloxy or halide.

11. The copolymer of item 9, wherein A3 is:

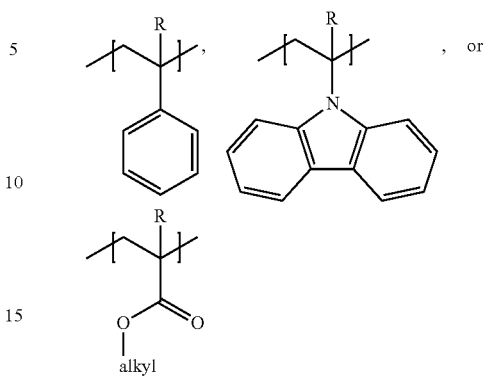

wherein R is hydrogen, methyl or ethyl.

12. The copolymer of any one of items 1 to 10, wherein A4 comprises a pendant group comprising a carboxylic acid group or a phosphoric acid group.
13. The copolymer of any one of items 1 to 11, wherein A4 is of formula:

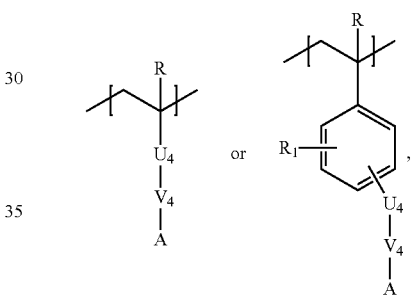

wherein R is hydrogen, methyl or ethyl,
R$_1$ is absent or represents one to four alkyl substituents; the alkyl substituents optionally comprising one or more ether, ester, amine, amide, urea, piperazinyl, sulfonamide, or carbamate functional groups,
U$_4$ is absent or represents an amide or ester linker,
V$_4$ is absent or represents alkyl optionally comprising one or more ether, ester, amine, amide, urea, piperazinyl, sulfonamide or carbamate functional group, and
A is —COOH, —PO(OH)$_2$,

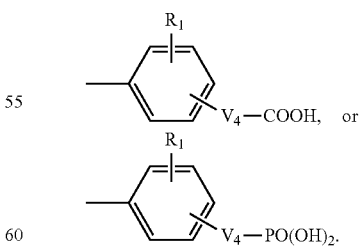

14. The copolymer of any one of items 1 to 12, wherein A4 is a monomer unit obtained by polymerizing acrylic acid, methacrylic acid, 4-carboxyphenylmethacrylamide, 4-carboxyphenylacrylamide, vinyl benzoic acid, vinyl phosphoric acid, methacrylyl alkyl phosphoric acid, or acrylyl alkyl phosphoric acid monomers.

15. A near-infrared radiation-sensitive coating composition comprising:
    a copolymer as defined in any one of items 1 to 13;
    a binder resin;
    a near-infrared radiation-absorbing compound; and
    optional additives.
16. A positive-working thermal lithographic printing plate comprising a near-infrared radiation-sensitive coating, the coating being a coating prepared from the coating composition of item 14.
17. A positive-working thermal lithographic printing plate comprising a near-infrared radiation-sensitive coating, the coating comprising:
    a copolymer as defined in any one of items 1 to 13;
    a binder resin;
    a near-infrared radiation-absorbing compound; and
    optional additives.
18. A method of producing a positive-working thermal lithographic printing plate, the method comprising the steps of:
    a) providing a substrate, and
    b) coating the coating composition of item 14 on the substrate.
19. A method of printing, the method comprising the steps of:
    a) providing a positive-working thermal lithographic printing plate according to item 15 or 16,
    b) imaging the printing plate with near-infrared radiation,
    c) developing the printing plate, and
    d) using the printing plate on a printing press to print.
    e) using the printing plate on a printing press to print.
20. A monomer corresponding to a monomer unit A1 as defined in any one of items 1 to 3.
21. A monomer corresponding to a monomer unit A2 as defined in any one of items 1 and 4 to 7.
22. A monomer corresponding to a monomer unit A3 as defined in any one of items 1 and 9 to 11.
23. A monomer corresponding to a monomer unit A4 as defined in any one of items 1, 12, and 13.

DETAILED DESCRIPTION OF THE INVENTION

Copolymers for Positive-Working Thermal Lithographic Printing Plates

Turning now to the invention in more details, there is provided a copolymer comprising monomer units A1, which are monomer units comprising a cyano-containing pendant group in which the cyano is not directly attached to the backbone of the copolymer and at least one other type of monomer units.

As used herein, a "copolymer" is a polymer made of at least two different types of monomer units. Such monomer units are relatively small molecules linked with relatively large numbers of other monomer units to form a chain, i.e. a polymer or copolymer. As used herein, the "backbone" of a polymer or copolymer means the series of covalently bonded atoms from the monomer units that together create the continuous chain of the polymer or copolymer. A "pendant group" is a group of atoms attached to, but not part of, the backbone of the copolymer.

As such then, a "cyano-containing pendant group" is a pendant group that comprises a cyano (—C≡N) group. Thus, in the above, the cyano group, which is comprised in a pendant group, is not directly attached to the backbone of the copolymer; it is rather attached to the pendant group, which is in turns attached to the backbone as in the more specific embodiments shown below. More specifically, the monomer unit having a cyano group containing pendant group cannot be

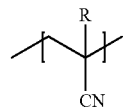

wherein R is any pendant group. Rather, this monomer unit may be of formula

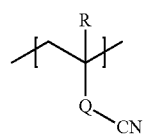

wherein R and Q are any pendant groups.

Herein, a "monomer" is a compound that becomes a monomeric unit upon polymerization. For example,

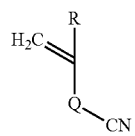

is the monomer producing monomeric unit

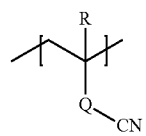

in a polymer or copolymer.

The copolymer is for use in near-infrared radiation-sensitive coating compositions for positive-working thermal lithographic printing plates. In embodiments, the copolymer may be a high-molecular weight copolymer, i.e. a copolymer with a molecular weight of 10,000 g/mol and more.

In embodiments, the copolymer has the general structure:

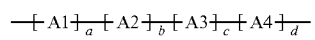

wherein a, b, and d are molar ratios varying between about 0.01 and about 0.90 and c is a molar ratio varying between about 0 and about 0.90, A1 represents monomer units comprising a cyano-containing pendant group in which the cyano is not directly attached to the backbone of the copolymer;

A2 represents monomer units comprising two or more hydrogen bonding sites;

A3 represents monomer units that increase solubility in organic solvents; and

A4 represents monomer units that increase solubility in aqueous alkaline solutions.

It is to be understood from the above general structure that the copolymer can simultaneously comprise two or more different A1 monomer units, two or more different A2 monomer units, two or more different A3 monomer units and/or two or more different A4 monomer units.

In the above, c can be 0, which means that A3 is optional. Thus, in embodiments, A3 is absent from the above chemical structure. In other embodiments, c varies between about 0.01 and about 0.90. In embodiments, a, b, c, and/or d are 0.1, 0.2, 0.3, 0.4, 0.5, 0.6, 0.7, or 0.8 or more and/or are 0.8, 0.7, 0.6, 0.5, 0.4, 0.3, 0.2, 0.1 or less.

In embodiments, A1 is of formula:

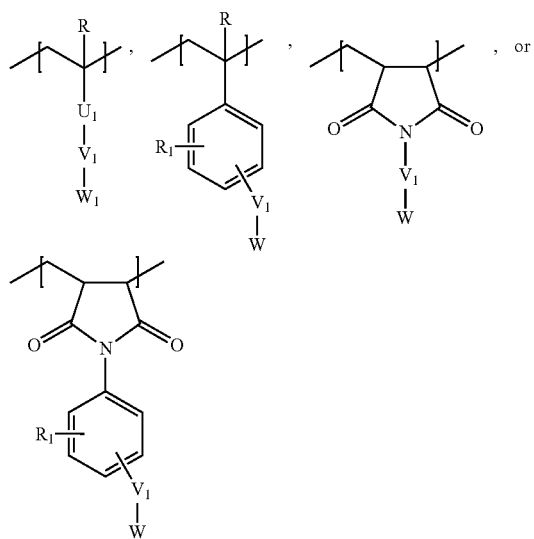

wherein:
R is hydrogen, methyl or ethyl,
$R_1$ is absent or represents one to four alkyl or alkoxy substituents; the alkyl substituents optionally comprising one or more ether, ester, amine, amide, urea, piperazinyl, sulfonamide, or carbamate functional groups, the alkyl substituents optionally being substituted with one or more cyano,
$U_1$ is an amide or ester linker,
$V_1$ is absent or represents alkyl optionally comprising one or more ether, ester, amine, amide, urea, piperazinyl, sulfonamide or carbamate functional group, the alkyl optionally being substituted with one or more cyano, and
W is —CN or

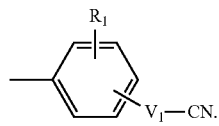

Herein, when it is said that an alkyl comprises (or optionally comprises) a functional group, it means that the functional group may be either at end of the alkyl or in between any two carbon atoms of the alkyl. For more certainty, when more than one functional group is comprised in an alkyl, the functional groups do not need to be separated by carbon atoms of the alkyl; i.e. they may be directly attached to one another. It is understood that when such a functional group (having two available bonds as shown below) is located at an end of the alkyl, one of its two available bonds will be attached to the terminal carbon atom of the alkyl and the other will be attached to a hydrogen atom.

Herein, when it is said that an alkyl is substituted (or optionally substituted) with a group, this expression has its regular meaning in the art, i.e. one of the hydrogen atoms of the alkyl is replaced by the group.

For more certainty, herein an ether functional group is —O—; an ester functional group (or linker) is —(C=O)—O— or —O—(C=O)—; an amine functional group is —$NR_3$—, an amide functional group (or linker) is —(C=O)—$NR_3$— or —$NR_3$—(C=O)—; an urea functional group is —$NR_3$—(C=O)—$NR_3$—; a piperazinyl functional group is

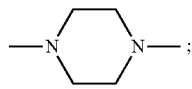

a sulfonamide functional group is —$SO_2$—$NR_3$— or —$NR_3$—$SO_2$—; and a carbamate functional group is —$NR_3$—(C=O)—O— or —O—(C=O)—$NR_3$—. In these functional groups, $R_3$ is hydrogen or alkyl, the alkyl being optionally substituted with one or more hydroxy, alkyloxy or halide.

In embodiments, A1 is

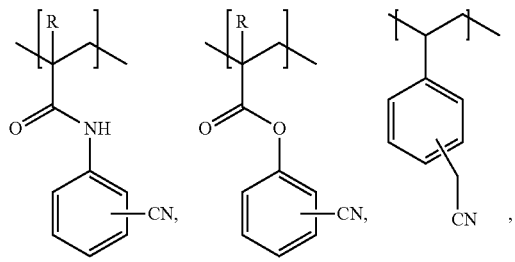

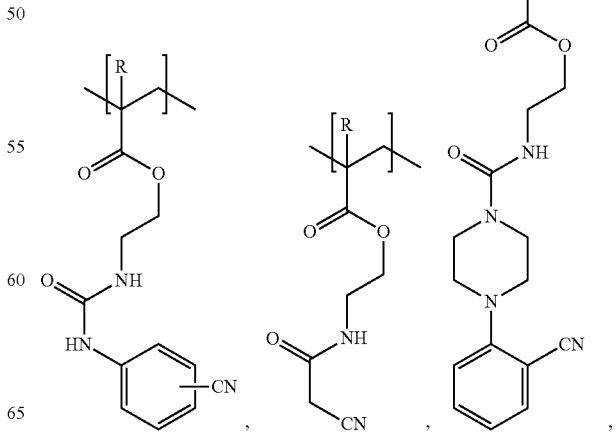

-continued

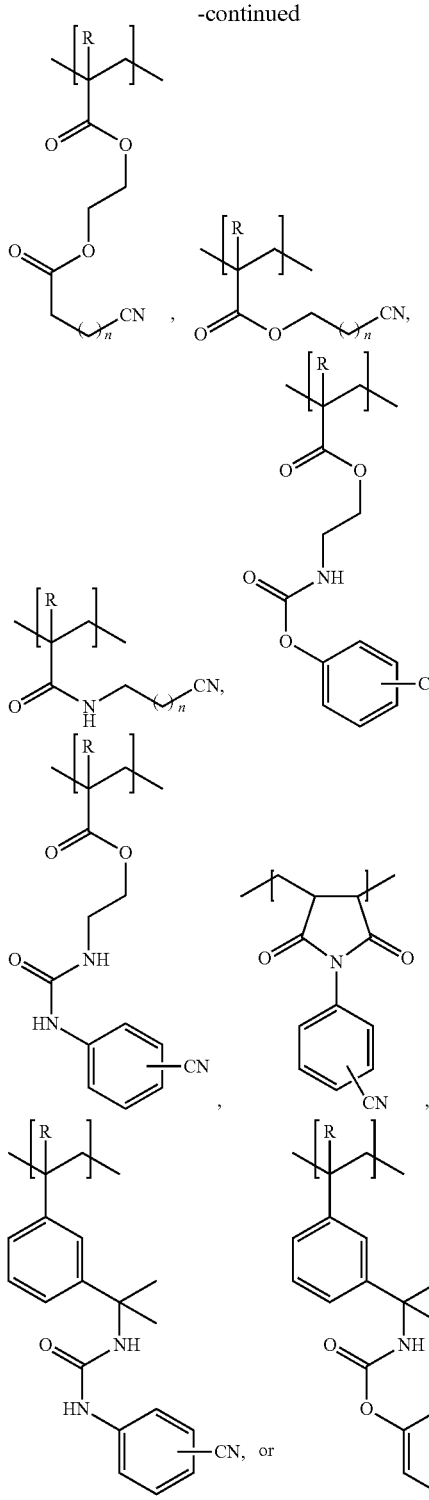

wherein R is hydrogen, methyl or ethyl and n varies between 1 and 10.

In a related aspect, the present invention also relates to monomers. More specifically, the present invention relates to monomers corresponding to any and all of the above-described A1 monomer units, individually or together as a group, as well as to any and all subsets thereof.

For the sake of concision, the formulas of these monomers are not repeated here. The skilled person will easily infer these formulas from the formulas of the A1 monomer units given above. Indeed, as used herein, a "monomer" is a compound that becomes a monomeric unit upon polymerization. For example,

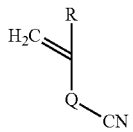

is the monomer producing monomeric unit

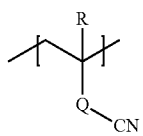

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

As stated above, A2 is a monomer unit comprising two or more hydrogen bonding sites. In embodiments, A2 comprises three, four or five hydrogen bonding sites. A2 comprises functional groups capable of forming hydrogen bonds. Such functional groups are well-known to persons of skill in the art and include groups containing a hydrogen atom in a polar covalent bond and groups containing an electronegative atom with a pair of free electrons. Non-limiting examples of such groups include hydroxy, carboxy, esters, amines, amides and groups obtained by combining any of them.

In specific embodiments, A2 is of formula:

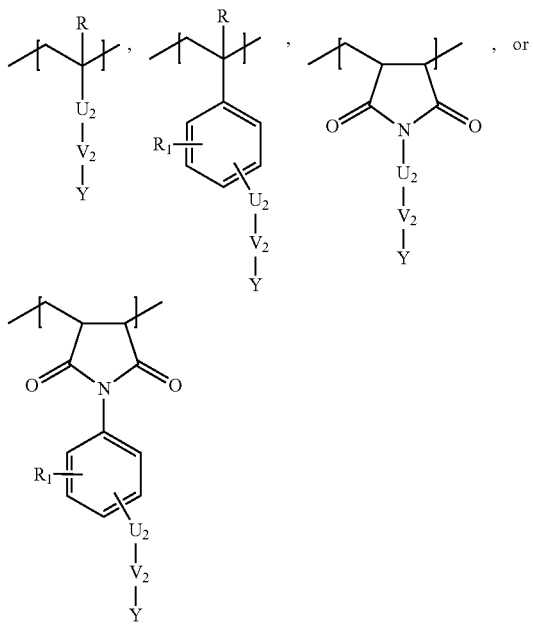

wherein:

R is hydrogen, methyl or ethyl, $R_1$ is absent or represents one to four alkyl substituents, the alkyl substituents optionally comprising one or more ether, ester, amine, amide, urea, piperazinyl, sulfonamide, or carbamate functional groups, $U_2$ is absent or represents an amide or ester linker, $V_2$ is absent or represents alkyl optionally comprising one or more ether, ester, amine, amide, urea, piperazinyl, sulfonamide or carbamate functional group, and Y is —OH, —$SO_2$—NH—$R_2$,

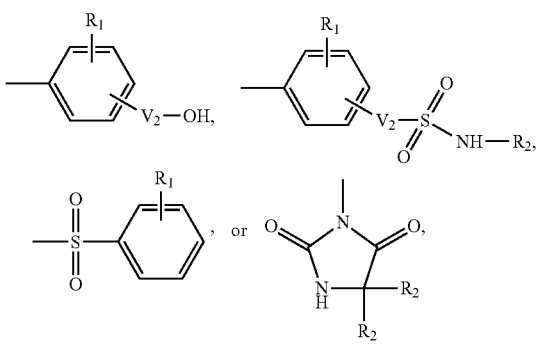

wherein $R_2$ each time it appears is independently hydrogen or alkyl optionally comprising one or more ether, ester, amine, amide, urea, piperazinyl, sulfonamide, or carbamate functional group.

In embodiments, A2 comprises a pendant group comprising a 5,5-dialkylhydantoin such as 5,5-dimethylhydantoin group (i.e.

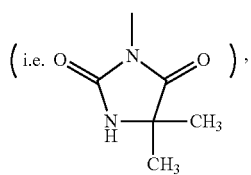

an aminosulfonamide group (such as —NH—$C_6H_4$—$SO_2$—$NH_2$), or hydroxy group.

In embodiments, A2 is

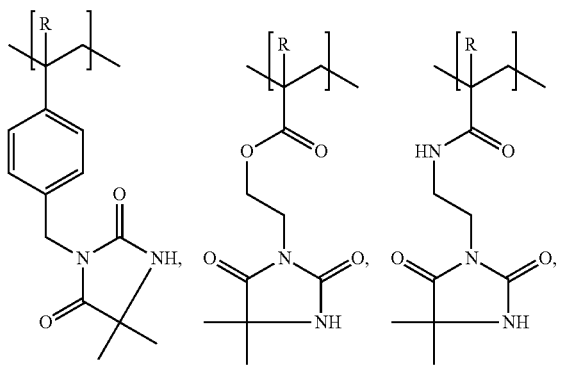

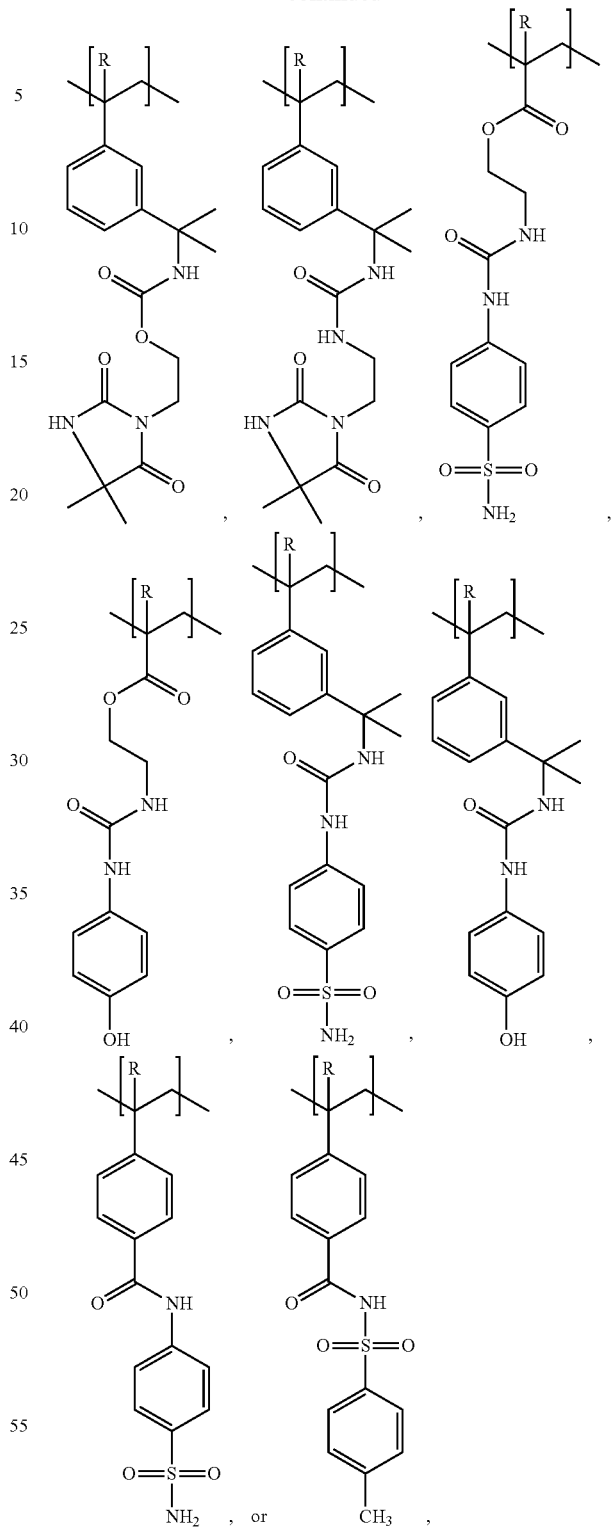

wherein R is hydrogen, methyl or ethyl.

In a related aspect, the present invention also relates to monomers. More specifically, the present invention relates to monomers corresponding to any and all of the above-described A2 monomer units, individually or together as a group, as well as to any and all subsets thereof.

For the sake of concision, the formulas of these monomers are not repeated here. The skilled person will easily infer these formulas from the formulas of the A2 monomer units given above. Indeed, as used herein, a "monomer" is a compound that becomes a monomeric unit upon polymerization. For example,

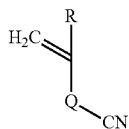

is the monomer producing monomeric unit

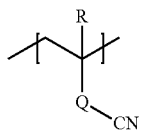

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

As stated above, A3 is a monomer unit that increases in organic solvents. The organic solvents include those typically used in the manufacture of thermal lithographic printing plates; for example: alcohol, ketone, N,N,-dimethylformamide, N-methyl-2-pyrrolidone, 1,3-dioxolane and other common polar solvents.

In embodiments, A3 comprises an alkyl or aryl pendant group. The alkyl and aryl groups increase solubility in organic solvents. The solubility of the copolymer can thus be modulated by varying molar ratio c.

In embodiments, A3 is of formula:

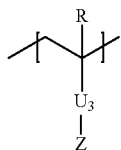

wherein
R is hydrogen, methyl or ethyl,
$U_3$ is absent or represents an amide or ester linker, and
Z is alkyl or aryl, the alkyl being optionally substituted with one or more hydroxy, alkyloxy or halide and the aryl being optionally substituted with one or more alkyls that are optionally substituted with one or more hydroxy, alkyloxy or halide.
In embodiments, Z is carbazole

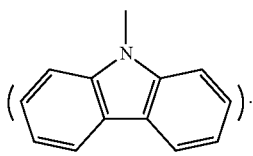

In embodiments, A3 is:

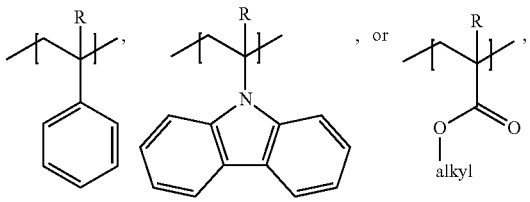

wherein R is hydrogen, methyl or ethyl.

In a related aspect, the present invention also relates to monomers. More specifically, the present invention relates to monomers corresponding to any and all of the above-described A3 monomer units, individually or together as a group, as well as to any and all subsets thereof.

For the sake of concision, the formulas of these monomers are not repeated here. The skilled person will easily infer these formulas from the formulas of the A3 monomer units given above. Indeed, as used herein, a "monomer" is a compound that becomes a monomeric unit upon polymerization. For example,

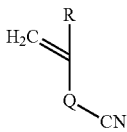

is the monomer producing monomeric unit

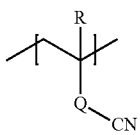

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

As stated above, A4 increases solubility in aqueous alkaline solutions. Thus, A4 typically comprises a pendant group comprising an acidic functional group, such as a carboxylic acid (—COOH) or a phosphoric acid (—PO(OH)$_2$). These acidic functional groups increase solubility in aqueous alkaline solutions. The solubility of the copolymer can thus be modulated by varying molar ratio d.

In specific embodiments, A4 is of formula:

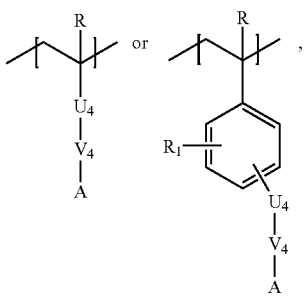

wherein R is hydrogen, methyl or ethyl,

R₁ is absent or represents one to four alkyl substituents; the alkyl substituents optionally comprising one or more ether, ester, amine, amide, urea, piperazinyl, sulfonamide, or carbamate functional groups, U₄ is absent or represents an amide or ester linker, V₄ is absent or represents alkyl optionally comprising one or more ether, ester, amine, amide, urea, piperazinyl, sulfonamide or carbamate functional group, and A is —COOH, —PO(OH)₂,

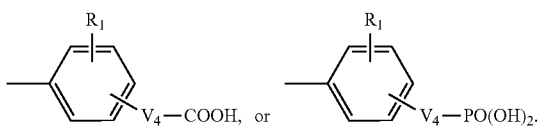

In embodiments, A4 is a monomer unit obtained by polymerizing acrylic acid, methacrylic acid, 4-carboxyphenylmethacrylamide, 4-carboxyphenylacrylamide, vinyl benzoic acid, vinyl phosphoric acid, methacrylyl alkyl phosphoric acid, or acrylyl alkyl phosphoric acid monomers.

In a related aspect, the present invention also relates to monomers. More specifically, the present invention relates to monomers corresponding to any and all of the above-described A4 monomer units, individually or together as a group, as well as to any and all subsets thereof.

For the sake of concision, the formulas of these monomers are not repeated here. The skilled person will easily infer these formulas from the formulas of the A4 monomer units given above. Indeed, as used herein, a "monomer" is a compound that becomes a monomeric unit upon polymerization. For example,

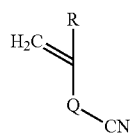

is the monomer producing monomeric unit

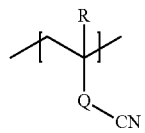

in a polymer or copolymer. The skilled person will easily appreciate that the monomer corresponding to any given monomeric unit will be identical to that monomeric unit except that the two bonds linking the monomeric unit to two other monomer units (to the left and to the right in the above formula) are replaced by a double bond.

Methods of Making Copolymers

The copolymers of the invention typically have reduced toxicity and are easy and inexpensive to manufacture. They can be obtained by copolymerizing the corresponding monomers in organic solvents using free radical initiators. Examples of such initiators include 2,2'-azobis(2-methylbutyronitrile), benzoyl peroxide, and ammonium persulfate. The resulting copolymers are then isolated by precipitation in water or mixtures of water and alcohol, filtered and dried until constant weight.

Near-Infrared Radiation-Sensitive Coating Compositions for Positive-Working Thermal Lithographic Printing Plates In another aspect, the present invention relates to the use of the above-described copolymers in near-infrared radiation-sensitive coating compositions for single- or multiple-layer positive-working thermal lithographic printing plates. Such plates can be directly imaged with near-infrared laser imaging devices in computer-to-plate and digital offset printing technologies.

Thus, the present invention relates to a near-infrared radiation-sensitive coating composition for a positive-working thermal lithographic printing plate, the composition comprising:

a copolymer as defined above, preferably in an amount between about 15 and about 85% by weight;

a binder resin, preferably in an amount between about 15 and about 85% by weight;

a near-infrared radiation-absorbing compound, preferably in an amount between about 1.0 and about 15% by weight; and optional additives, preferably in an amount between amount 0.50 and about 2.0% by weight.

It is to be understood from the above that the coating composition may comprise a mixture of copolymers, a mixture of binder resins, a mixture of near-infrared radiation-absorbing compounds, and/or a mixture of optional additives, such as visible colorants, film-forming additives and stabilizers.

Such coating compositions can be used to prepare a coating for a positive-working thermal lithographic printing plate. The coating composition is radiation-sensitive in that, upon exposure to radiation, there will be a physical or chemical process in the coating (produced using the coating composition) so that 1) the imaged areas will be different from the non-imaged areas after exposure to radiation and 2) development will produce an image on the printing plate.

Binder Resins

According to the present invention, the coating composition comprises binder resins, preferably in an amount between about 15-20% and about 80-85% by weight. Suitable binder resins for use in positive-working thermal lithographic printing plates are well known to the skilled person.

Examples of binder resins include polymers and copolymers comprising hydroxy groups that can form a hydrogen bonding network with the copolymers of the invention. Such binder resins are, for example, phenolic resins, acetal copolymers and cellulosic polymers. In embodiments, the binder resin is Thermolak® 7525 (a phenolic resin, available from American Dye Source, Inc., Baie d'Urfe, Quebec, Canada), Thermolak® 0802 (an acetal copolymer, available from American Dye Source, Inc., Baie d'Urfe, Quebec, Canada) and cellulose acetate hydrogen phthalate (available from Kodak, Kingsport, Tenn., USA).

Near-Infrared Radiation-Absorbing Compound

According to the present invention, the coating composition further comprises a near-infrared radiation-absorbing compound, preferably in an amount between about 1.0 and about 15% by weight. Suitable near-infrared radiation-absorbing compounds for use in positive-working thermal lithographic printing plates are well known to the skilled person. Such near-infrared radiation-absorbing compounds have one or more absorption bands between about 780 and about 1,100 nm. These materials convert incoming near-infrared radiation into heat.

Suitable near-infrared absorbing compounds are, for example, cyanine molecular and merocyanine dyes, such as that described in U.S. Pat. Nos. 5,397,690 and 6,326,122, which are incorporated herein by reference. Other examples of near-infrared absorbing molecular dyes include the following, which available from American Dye Source, Inc., Baie d'Urfe, Quebec, Canada:

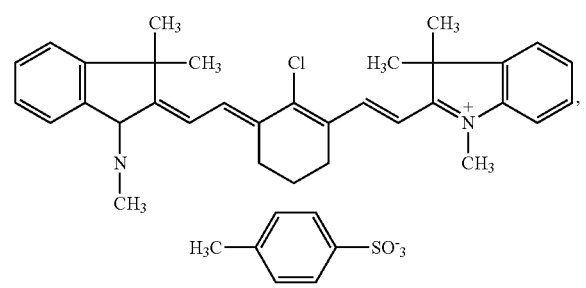

ADS780AT

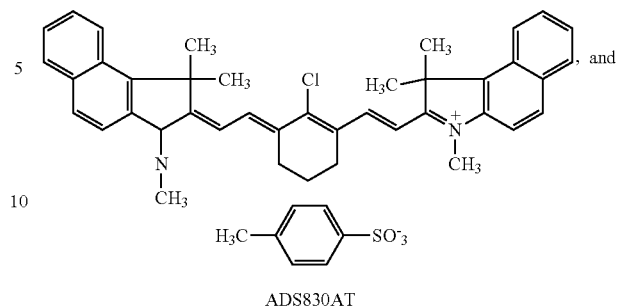

ADS830AT

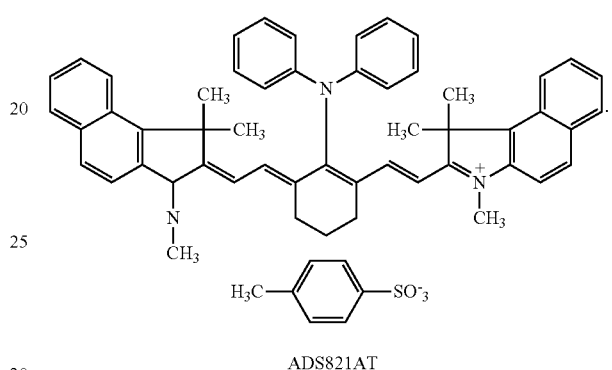

ADS821AT

Other suitable near-infrared absorbing compounds are the polymers described in U.S. Pat. Nos. 6,124,425; 6,177,182; and 7,473,515, which are incorporated herein by reference. Yet other suitable near-infrared absorbing polymers are available from American Dye Source, Inc., Baie d'Urfe, Quebec, Canada, and have the following structures:

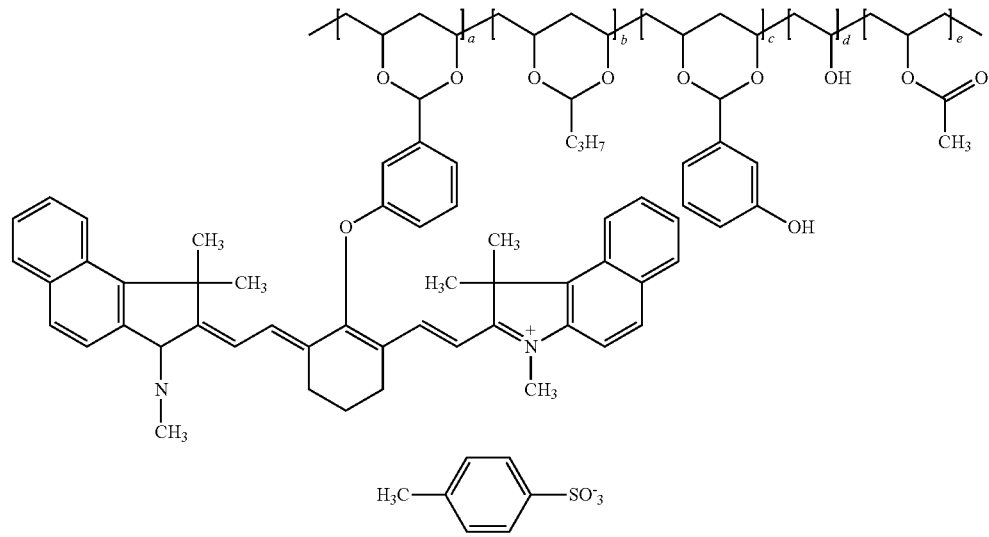

Thermolak® 8010 wherein a, b, c, d, and e are the molar ratios, which are 0.10, 0.30, 0.50, 0.08 and 0.02, respectively; and

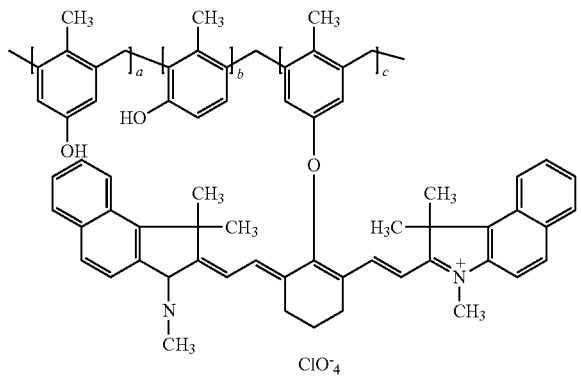

Thermolak ® 1010 wherein a, b, and c are the molar ratios, which are 0.73, 0.25, and 0.02 respectively.

The amount of such near-infrared radiation-absorbing polymers in the coating composition is preferably between about 7 and about 15 weight percent.

Another near-infrared radiation-absorbing materials that can be used in the coating composition of the present invention may be the near-infrared radiation-absorbing gallotannic compounds described in U.S. Provisional Patent Application 61/255,918, which is incorporated herein by reference. These compounds are available from American Dye Source, Inc., Baie d'Urfe, Quebec, Canada. One example of such gallotannic compound is:

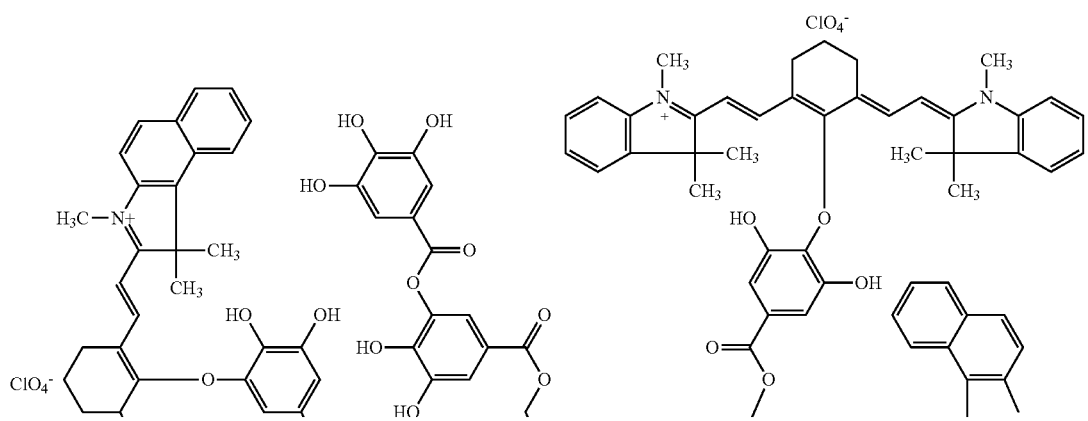

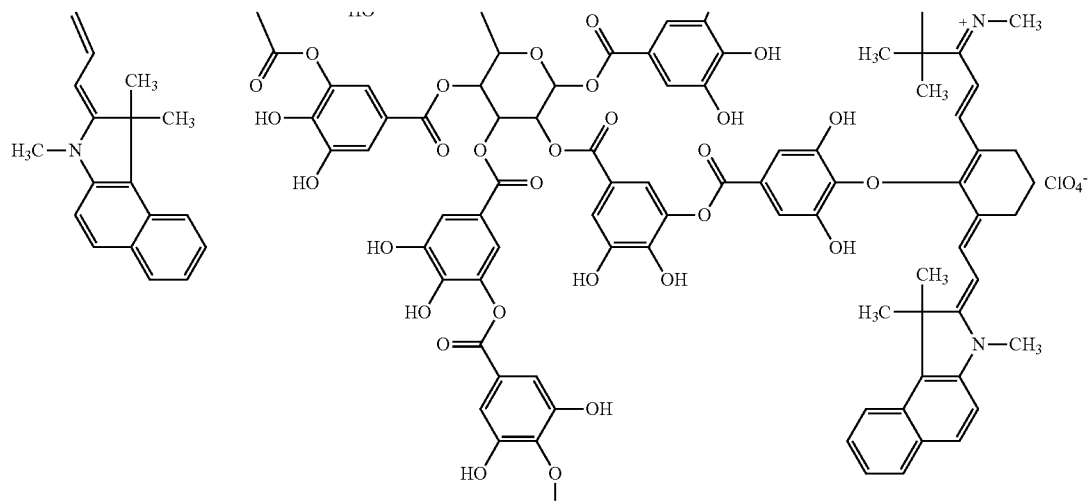

-continued

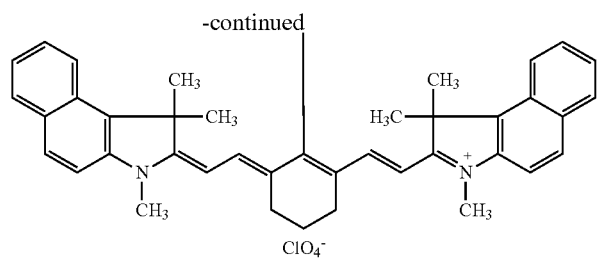

Thermolak® 9031.

The amount of such near-infrared radiation-absorbing gallotannic compounds is preferably between about 2 and about 5 weight percent.

Optional Additives

The optional additives that can be used in the above-described coating composition include, for example, visible colorants, film-forming agents and shelf-life stabilizers. Such additives and their use are well known to the persons of skill in the art.

In embodiments, visible colorants having absorption bands between 450 and 780 nm are used, preferably in an amount between about 1 and about 5 weight percent. Examples of such visible colorants include cationic dyes, such as basic blue 3, basic blue 7, basic blue 11, basic blue 17, basic blue 26, basic blue 66, basic red 9, basic red 29, basic violet 2, basic violet 3, basic violet 4, basic violet 6, basic violet 14, basic green 4 and basic green 5.

The coating composition may further comprise film-forming agents to provide more uniformly coated films and to provide a more slippery top surface so as to reduce the formation of scratches during handling and packaging. Examples of film-forming agents include siloxane copolymers having polyether, polyester and alkyl pendant groups, such as that commercially available from BYK USA (Wallingford, Conn., USA) under trade names BYK 306, BYK 307, BYK 310, BYK 333, and BYK 337. Another suitable film-forming agent is a siloxane copolymer comprising polyether and alkyl pendant groups available from American Dye Source, Inc. under trade name Thermolak® P1000S. The amount of film-forming agents in the coating compositions is preferably between about 1 and about 6 weight percent.

The coating composition may further comprise shelf-life stabilizers such as that described in U.S. Pat. No. 6,884,568, including 3-mercapto-1,2,4-triazole; 3-mercapto-4-methyl-4H-1,2,4-triazole; 3-mercapto-5-(4-pyridyl)-1H-1,2,4-triazole; 2-mercaptobenzimidazole; 2-mercaptobenzoxazole; 2-mercaptobenzothiazole; 6-ethoxy-2-mercaptobenzothiazole; 2-mercapto-5-methyl-1,3,4-thiadiazole; 2-mercapto-5-phenyl-1,3,4-oxadiazole; 2-mercapto-5-(4-pyridyl)-1,3,4-oxadiazole; 5-mercapto-3-methylthio-1,2,4-thiadiazole; 2-mercapto-5-methylthio-1,3,4-thiadiazole; 2-mercaptoimidazole; 2-mercapto-1-methylimidazole; 5-mercapto-1-methyl-1H-tetrazole; and 5-mercapto-1-phenyl-1H-tetrazole. The amount of thermal stabilizers in the coating compositions is preferably between about 1 and about 4 weight percent.

The coating composition may also comprise one or more suitable solvents. The solvent allows for the formation of a coating on a substrate. Any solvent known to the person of skill in the art to be appropriate for this purpose can be used. Non-limiting examples of such solvent include n-propanol, isopropanol, 2-methoxy propanol, ethyl glycol, water or a mixture thereof.

Positive-Working Thermal Lithographic Printing Plates and Methods of Producing and Using In another aspect, the present invention relates to a positive-working thermal lithographic printing plate comprising a near-infrared radiation-sensitive coating, the coating being a coating prepared from the above-described coating composition.

In another related aspect, the present invention relates to a positive-working thermal lithographic printing plate comprising a near-infrared radiation-sensitive coating, the coating comprising:
  a copolymer as defined above;
  a binder resin as defined above;
  a near-infrared radiation-absorbing compound as defined above; and
  optional additives as defined above.

In the printing plate, the near-infrared radiation-sensitive coating is deposited on a substrate. In embodiments, the substrate is anodized aluminum, plastic films or paper. Aluminum substrates may be brushed-grained or electro-grained, then anodized with acidic solutions. The near-infrared radiation-sensitive coating may have a coating weight between about 1.0 and about 3.0 g/m².

In embodiments, there may be one or more layers between the substrate and the near-infrared radiation-sensitive coating and/or on top of the near-infrared radiation-sensitive coating as known to the person of skill in the art. For example, a polymeric adhesion-promoting and/or heat-insulating layer may be present between the substrate and the near-infrared radiation-sensitive coating. This layer may be obtained from aqueous solutions containing poly(acrylic acid), poly(acrylic acid-co-vinylphosphoric acid) or polyvinyl phosphoric acid, which are then dried using hot air at about 110° C. The coating weight of the adhesion-promoting and/or heat-insulating layer may be between about 0.1 and about 1.0 g/m². Overcoat layers can also be provided on top of the near-infrared radiation-sensitive coating. Such layers typically protect the near-infrared radiation-sensitive coating from deleterious ambient radiation, humidity, scratching, sticking, etc.

In another related aspect, the present invention relates to a method of producing a positive-working thermal lithographic printing plate, the method comprising the steps of: a) providing a substrate, and b) coating a coating composition as defined above on the substrate. In embodiments, the method further comprises the step of coating the substrate with a polymeric adhesion-promoting and/or heat insulating layer before step b).

In another related aspect, the present invention relates to a method of printing, the method comprising the steps of: a)

providing a positive-working thermal lithographic printing plate as defined above, b) imaging the printing plate with near-infrared radiation, c) developing the printing plate and d) using the printing plate on a printing press to print. The printing plates may be directly imaged with laser imaging devices in computer-to-plate and digital offset printing technologies. In embodiments, the imaged plate is developed off press with water or a developer.

In use, the copolymer and the binder in the coating will produce a cohesive network by forming hydrogen bonds. Upon exposure to near-infrared radiation, the near-infrared radiation-absorbing compound will absorb the incoming near-infrared radiation and produce heat. The heat will disrupt the hydrogen bond network in the imaged areas. This will make the exposed areas more soluble in water or developer (off-press development) or fountain solution and inks (on-press development) than the unexposed areas, which will remain less soluble. This will allow the development (on- or off-press) of the printing plates.

Some of the compounds described herein may exist as isomers of different types (optical, geometric and/or positional isomers for example). The present invention embraces all such isomers.

Unless otherwise noted, as used herein "alkyl" means a linear or branched alkyl group having 1 to 24 carbon atoms and "aryl" means an aryl group having 1 to 3 cycles and optionally comprising one or two heteroatoms, such as N, O and S. Similarly, "alkyloxy" means a linear or branched alkyloxy (R—O—) group comprising 1 to 24 carbon atoms.

Herein, "halide" means F—, Cl—, Br— or I—.

Herein, unless otherwise indicated, weight percent values are based on the total dry weight of the coating composition.

As used herein, "near-infrared radiation" means electromagnetic radiation, such as that emitted by a laser, with a wavelength between about 700 and about 1100 nm. Non-limiting examples of such near-infrared radiation is the light emitted by diode lasers, which are equipped with platesetters available from Creo-Kodak, Dinippon Screen, Heidelberg and Presstek International.

As used herein, "about" means plus or minus 5% of the numerical value thus qualified.

Other objects, advantages and features of the present invention will become more apparent upon reading of the following non-restrictive description of specific embodiments thereof, given by way of example only with reference to the accompanying drawings.

Description of Illustrative Embodiments

The present invention is illustrated in further details by the following non-limiting examples. These examples use the compounds listed in the following glossary.

Glossary

| | |
|---|---|
| Basic violet 3 | Visible colorant, available from Spectra Colors, Kearny, New Jersey, USA. |
| DMF | N,N-dimethylformamide |
| Dowanol PM | 2-Methoxy propanol, available from Dow Chemicals, USA and Ho Chi Minh City, Vietnam. |
| EMA | Ethyl methacrylate, available from Sigma Aldrich, Canada. |
| GSP90 | Aqueous alkaline developer for positive-working thermal lithographic offset printing plates having a conductivity of 80 mS/cm at 25° C., available from Mylan Group, Travinh City, Travinh Province, Vietnam. |
| HDB-01 | 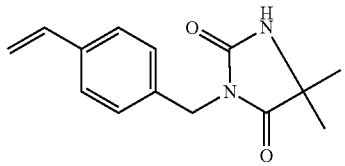 [SMILES: C=Cc1ccc(CN2C(=O)NC(C)(C)C2=O)cc1] 3-[4-Vinylbenzyl]-5,5-dimethylhydantoin, available from American Dye Source, Inc., Baie d'Urfe, Quebec, Canada. |
| HDB-02 | 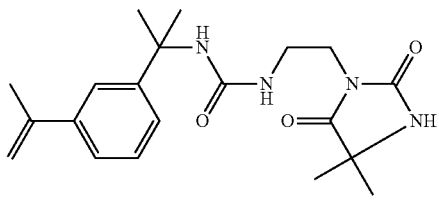 [SMILES: C=C(C)c1cccc(C(C)(C)NC(=O)NCCN2C(=O)NC(C)(C)C2=O)c1] 3-{2-Methyl-2[N-[(3-ethyl-5,5-dimethylhydantoinyl)ureido]ethyl}-2-methylvinyl benzene, available from American Dye Source, Inc., Baie d'Urfe, Quebec, Canada. |
| HDB-03 | 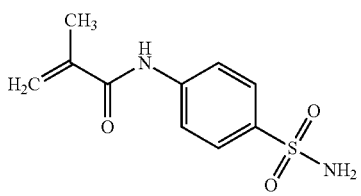 [SMILES: C=C(C)C(=O)Nc1ccc(S(N)(=O)=O)cc1] N-(4-aminosulfonylphenyl)methacrylamide, available from American Dye Source, Inc., Baie d'Urfe, Quebec, Canada. |

| | |
|---|---|
| HDB-04 | 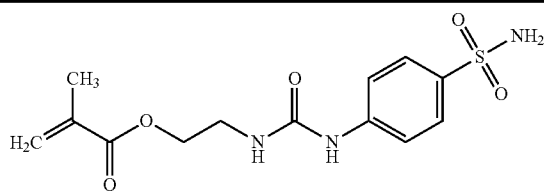 |
| | 2-[N'-(4-aminosulfonylphenyl)ureido]-ethylmethacrylate, available from American Dye Source, Inc., Baie d'Urfe, Quebec, Canada. |
| HDB-05 | 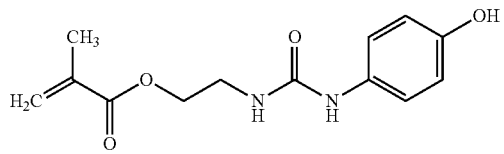 |
| | 2-[N'-(4-hydroxyphenyl)ureido]ethylmethacrylate, available from American Dye Source, Inc., Baie d'Urfe, Quebec, Canada. |
| HDB-06 | 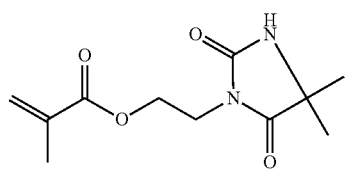 [SMILES: C=C(C)C(=O)OCCN1C(=O)NC(C)(C)C1=O] |
| | 2-(5,5-Dimethylhydantoinyl)ethyl methacrylate, available from American Dye Source, Inc., Baie d'Urfe, Quebec, Canada. |
| MCN-01 | 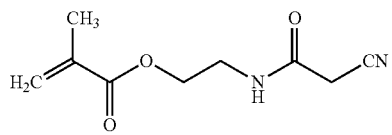 |
| | 2-(Cyanomethylamido)ethylmethacrylate available from American Dye Source, Inc., Baie d'Urfe, Quebec, Canada. |
| MCN-02 | 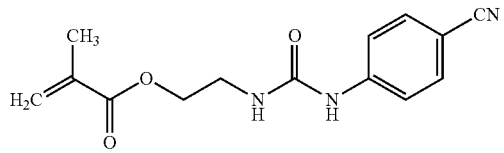 [SMILES: C=C(C)C(=O)OCCNC(=O)Nc1ccc(C#N)cc1] |
| | 2-[N'-(4-Cyanophenyl)ureido]ethylmethacrylate available from American Dye Source, Inc., Baie d'Urfe, Quebec, Canada. |
| MCN-03 | 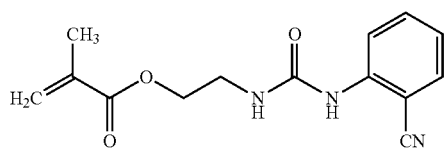 [SMILES: C=C(C)C(=O)OCCNC(=O)Nc1ccccc1C#N] |
| | 2-[N'-(2-Cyanophenyl)ureido]ethylmethacrylate available from American Dye Source, Inc., Baie d'Urfe, Quebec, Canada. |
| MCN-04 | 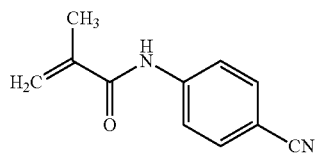 |
| | 4-Cyanophenyl methacrylamide, available from American Dye Source, Inc., Baie d'Urfe, Quebec, Canada. |
| MEK | Methyl ethyl ketone, available from Sigma Aldrich, Canada or from Sapa Chemicals, Ho Chi Minh City, Vietnam. |
| MMA | Methylmethacrylate, available from Sigma Aldrich, Canada. |

| | |
|---|---|
| NMP | N-methyl-2-pyrrolidone, available from Sapa Chemicals, Ho Chi Minh City, Vietnam. |
| PG Aqueous Solution | Aqueous solution containing 60% by weight of propylene glycol in water, available from Mylan Group, LongDuc Industrial Park, Travinh City, Travinh Province, Vietnam. |
| PM Aqueous Solution | Aqueous solution containing 60% by weight of propylene glycol methyl ether in water, available from Mylan Group, LongDuc Industrial Park, Travinh City, Travinh Province, Vietnam. |
| Stabilat-20 | An aqueous solution containing 20% by weight of Stabilat D2010, which is a concentrated fountain solution for sheet fed press available from FUJIFILM Hunt Chemicals Singapore Pte. Ltd., Singapore |
| Thermolak ® P1000S | Siloxane copolymer comprising polyether and alkyl pendant groups, available from American Dye Source, Inc., Baie d'Urfe, Quebec, Canada. |
| Thermolak ® 1010 | Near-infrared absorbing polymer having a maximum absorption peak at 800 nm in methanol solution, available from American Dye Source, Inc., Baie d'Urfe, Quebec, Canada. |
| Thermolak ® 7525 | Novolak resin, available from American Dye Source, Inc., Baie d'Urfe, Quebec, Canada. |
| V59 | 2,2'-azobis(2-methylbutyronitrile), available from Wako (USA). |

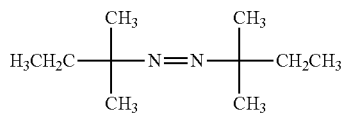

Synthesis of the Copolymers

The syntheses of the copolymers were performed in a 4 necks glass reactor equipped with a water condenser, a mechanical stirrer, a dropping funnel and a nitrogen gas inlet. The molecular structures of the obtained copolymers were determined by proton NMR and FTIR spectroscopy. The average molecular weight of the copolymers obtained was determined by size exclusion chromatography (SEC), using a N,N-dimethylformamide solution and calibrated with polystyrene standards. The acid number was determined by titration with a solution of potassium hydroxide in ethanol.

EXAMPLE 1

Copolymer PCN-01A having a general structure as shown below:

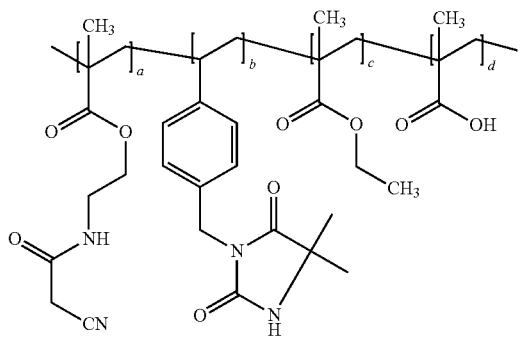

wherein a=0.20, b=0.37, c=0.35 and d=0.08 was synthesized by adding 0.30 grams of V59 into 120 ml of a DMF solution (in which 0.20 moles of MCN-01, 0.37 moles of HDB-01, 0.35 moles of ethyl methacrylate and 0.08 moles of methacrylic acid were dissolved) at 75° C. under constant stirring and nitrogen atmosphere. After 10 hours of polymerization, 0.20 grams of V59 was added into the reaction mixture and the polymerization was continued for another 14 hours. Air was introduced and the reaction mixture was stirred at 105° C. for an additional 2 hours to terminate the polymerization. The copolymer was precipitated in 2 L of de-ionized water, filtered and washed copiously with de-ionized water. A white powder was obtained after drying under vacuum at 40° C. The average molecular weight and acid number were determined to be 43,400 g/mole and 26.2 mg KOH/g, respectively.

EXAMPLE 2

Copolymer PCN-02A having a general structure as shown below:

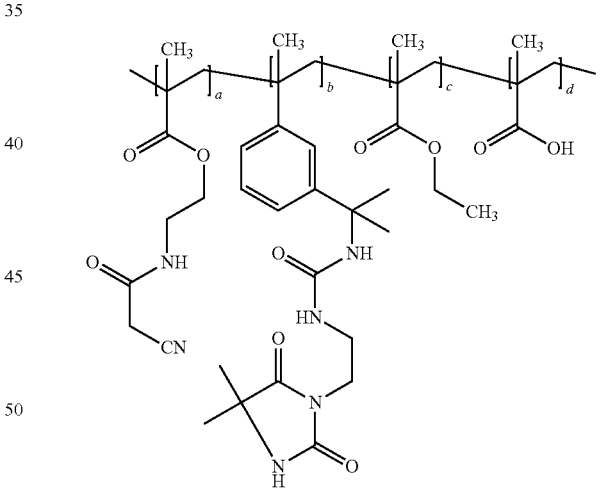

wherein a=0.20, b=0.37, c=0.35 and d=0.08 was synthesized by adding 0.30 grams of V59 into 120 ml of a DMF solution (in which 0.20 moles of MCN-01, 0.37 moles of HDB-02, 0.35 moles of ethyl methacrylate and 0.08 moles of methacrylic acid were dissolved) at 75° C. under constant stirring and nitrogen atmosphere. After 10 hours of polymerization, 0.20 grams of V59 was added into the reaction mixture and the polymerization was continued for another 14 hours. Air was introduced and the reaction mixture was stirred at 105° C. for an additional 2 hours to terminate the polymerization. The copolymer was precipitated in 2 L of de-ionized water, filtered and washed copiously with de-ionized water. A white powder was obtained after drying under vacuum at 40° C. The average molecular weight and acid number were determined to be 74,000 g/mole and 26.4 mg KOH/g, respectively.

EXAMPLE 3

Copolymer PCN-03A having a general structure as shown below:

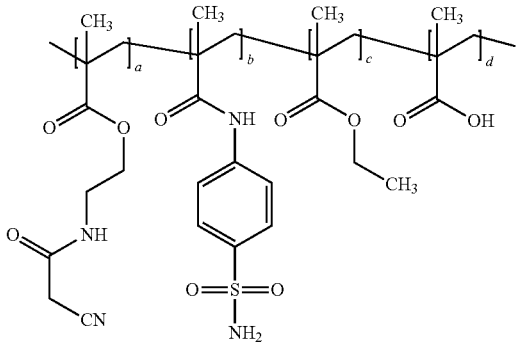

wherein a=0.20, b=0.37, c=0.35 and d=0.08 was synthesized similarly to Example 1 with the exception that 0.37 moles of HDB-03 replaced the HDB-01. After the polymerization, the copolymer was precipitated in 2 L of de-ionized water, filtered and washed copiously with de-ionized water. A white powder was obtained after drying under vacuum at 40° C. The molecular weight and acid number were determined to be 85,000 mole/g and 24.4 g/mole, respectively.

EXAMPLE 4

Copolymer PCN-04A having a general structure as shown below:

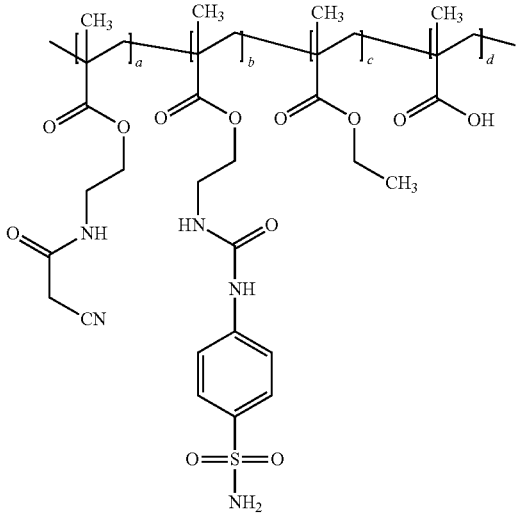

wherein a=0.20, b=0.37, c=0.35 and d=0.08 was synthesized similarly to Example 1 with the exception that 0.37 moles of HDB-04 replaced the HDB-01. After the polymerization, the copolymer was precipitated in 2 L of de-ionized water, filtered and washed copiously with de-ionized water. A white powder was obtained after drying under vacuum at 40° C. The molecular weight and acid number were determined to be 97,000 mole/g and 24.0 g/mole, respectively.

EXAMPLE 5

Copolymer PCN-05A having a general structure as shown below:

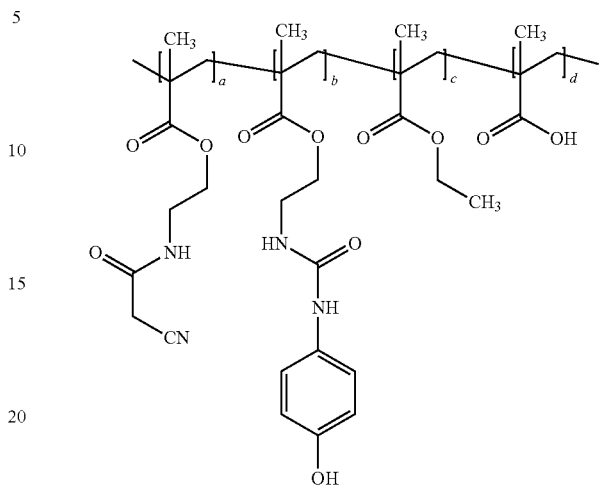

wherein a=0.20, b=0.37, c=0.35 and d=0.08 was synthesized similarly to Example 1 with the exception that 0.37 moles of HDB-05 replaced the HDB-01. After the polymerization, the copolymer was precipitated in 2 L of de-ionized water, filtered and washed copiously with de-ionized water. A white powder was obtained after drying under vacuum at 40° C. The molecular weight and acid number were determined to be 89,000 mole/g and 23.7 g/mole, respectively.

EXAMPLE 6

Copolymer PCN-06A having a general structure as shown below:

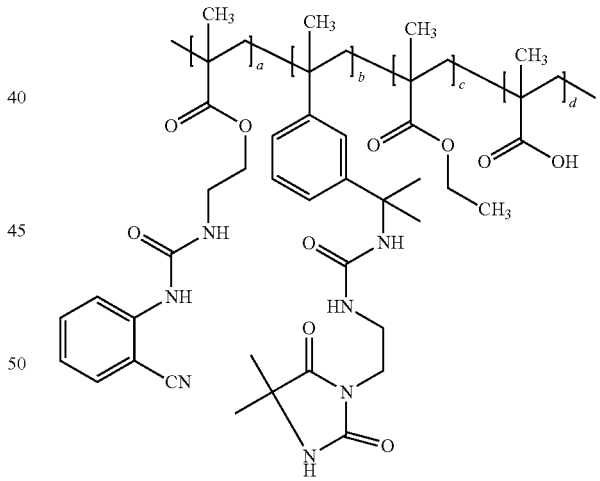

wherein a=0.20, b=0.37, c=0.35 and d=0.08 was synthesized by adding 0.30 grams of V59 into 120 ml of a DMF solution (in which 0.20 moles of MCN-02, 0.37 moles of HDB-02, 0.35 moles of ethyl methacrylate and 0.08 moles of methacrylic acid were dissolved) at 75° C. under constant stirring and nitrogen atmosphere. After 10 hours polymerization, 0.20 grams of V59 was added into the reaction mixture and the polymerization was continued for another 14 hours. Air was introduced and the reaction mixture was stirred at 105° C. for an additional 2 hours to terminate the polymerization. The copolymer was precipitated in 2 L of de-ionized water, filtered and washed copiously with de-ionized water. A white copolymer powder was obtained after drying under vacuum at 40° C. The average molecular weight and acid number were determined to be 67,000 g/mole and 23.6 mg KOH/g, respectively.

EXAMPLE 7

Copolymer PCN-07A having a general structure as shown below:

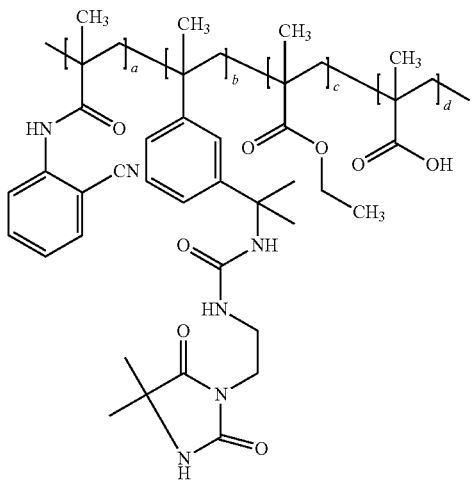

wherein a=0.20, b=0.37, c=0.35 and d=0.08 was synthesized similarly to Example 6 with the exception that the MCN-02 was replaced by 0.20 moles of MCN-04. After the polymerization, the copolymer was precipitated in 2 L of de-ionized water, filtered and washed copiously with de-ionized water. A white powder was obtained after drying under vacuum at 40° C. The molecular weight and acid number were determined to be 77,000 mole/g and 24.2 g/mole, respectively.

EXAMPLE 8

Copolymer PCN-08A having a general structure as shown below:

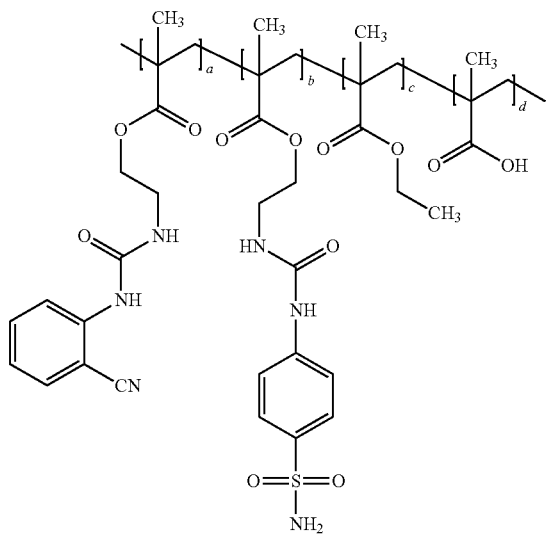

wherein a=0.20, b=0.37, c=0.35 and d=0.08 was synthesized by adding 0.30 grams of V59 into 120 ml of a DMF solution (in which 0.20 moles of MCN-02, 0.37 moles of HDB-04, 0.35 moles of ethyl methacrylate and 0.08 moles of methacrylic acid were dissolved) at 75° C. under constant stirring and nitrogen atmosphere. After 10 hours polymerization, 0.20 grams of V59 was added into the reaction mixture and the polymerization was continued for another 14 hours. Air was introduced and the reaction mixture was stirred at 105° C. for an additional 2 hours to terminate the polymerization. The copolymer was precipitated in 2 L of de-ionized water, filtered and washed copiously with de-ionized water. A white powder was obtained after drying under vacuum at 40° C. The average molecular weight and acid number were determined to be 105,000 g/mole and 23.9 mg KOH/g, respectively.

EXAMPLE 9

Copolymer PCN-09A having a general structure as shown below:

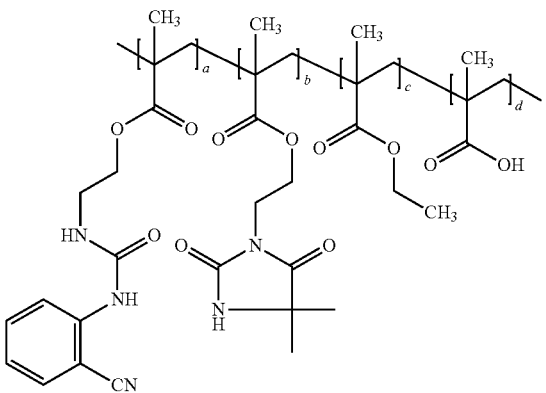

wherein a=0.20, b=0.37, c=0.35 and d=0.08 was synthesized similarly to Example 8 with the exception that 0.37 moles of HDB-06 were used to replace the HDB-04. After the synthesis, the copolymer was precipitated in 2 L of de-ionized water, filtered and washed copiously with de-ionized water. A white powder was obtained after drying under vacuum at 40° C. The average molecular weight and acid number were determined around 92,000 g/mole and 24.0 mg KOH/g, respectively.

EXAMPLE 10

Copolymer PCN-10A having a general structure as shown below:

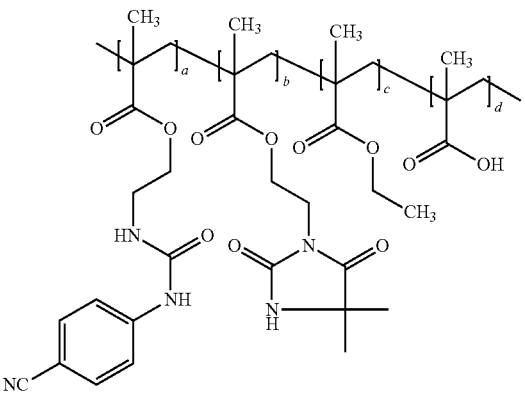

wherein a=0.20, b=0.37, c=0.35 and d=0.08 was synthesized similarly to Example 9 with the exception that 0.20 moles of MCN-03 were used to replace the MCN-02. After the synthesis, the copolymer was precipitated in 2 L of de-ionized water, filtered and washed copiously with de-ionized water. A white powder was obtained after drying under vacuum at 40° C. The average molecular weight and acid number were determined around 82,000 g/mole and 24.0 mg KOH/g, respectively.

Positive-Working Thermal Lithographic Offset Printing Plates

EXAMPLES 11 to 21

Coating solutions with the following compositions (Table I) were coated using a spin coater on aluminum substrate, which was electro-grained using a mixed acid solution i.e., hydrochloric acid and acetic acid, anodized in aqueous sulfuric acid solution, then post treated with aqueous NaF/NaH2PO$_4$ solution at 80° C. The coated films were dried at 100° C. with hot air. The obtained coating weight was around 1.7 g/m$^2$.

After being stored at 35° C. for 1 week, the plates were imaged using a PlateRite 8600S plate-setter (available from Screen, Japan) at a drum speed 900 RPM using different laser power. The imaged plates were developed using GSP90 developer with the TungSung 88 processor at 23° C.

The optical density of the printing plates was measured using a Shamrock Densitometer (Model: Color Print 415, available from Muller B.V., P.O. Box 44, 7913 ZG Holland-scheveld, Netherlands). The dot percentage on the developed plates was measured using a Techkon SpectroPlate measurement device (Model: Expert, available from Techkon USA LLC, Danvers, Mass. 01923, USA).

The printing tests were performed on the developed plates using a Heidelberg SpeedMaster 74 (Heidelberg, Germany) press using 24/7 sheetfed black ink (available from Toyo Ink, USA).

The chemical resistance tests were performed by dipping the developed plates in alcohol-water solutions and in concentrated fountain solution for 60 minutes at 25° C. The optical density of the plates before and after dipping in the alcohol solutions and fountain solution were recorded for calculation of the chemical resistance, which is denoted as CR.

Definitions

The Correct Exposure (CE, mJ/cm$^2$) is the imaging energy density requirement to have the 50% dot on the developed plate, which coincides with the 50% dot on the target.

The Clearing Point (CP, mJ/cm$^2$) is the energy density required to have the optical density at 0% dot equals the optical density at 100% dot time 0.05.

The Coating Development Lost (CDL, %) is calculated using the following equation:

$$CDL=[OD_{ad1}-OD_{sub}]/[OD_{bd1}-OD_{sub}]\times100$$

where:
$OD_{ad1}$ is the optical density at 100% dot after development;
$OD_{sub}$ is the optical density of the uncoated aluminum substrate; and
$OD_{bd1}$ is the optical density of 100% solid before development.

Smaller CE, CP and CDL values indicate better performances of the printing plate.

The chemical resistance (CR, %) was calculated using the change of optical density and the following equation:

$$CR=[OD_{ad2}-OD_{sub}]/[OD_{bd2}-OD_{sub}]\times100$$

where:
$OD_{ad2}$ is the optical density at 100% dot after development and then dipping in an alcohol solution for 30 minutes at 25° C.;
$OD_{sub}$ the optical density of the uncoated aluminum substrate; and
$OD_{bd2}$ is the optical density of 100% solid after development and before dipping in an alcohol solution.

TABLE I

|  | Ex. 11 | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|
| Ingredients | Weight (grams) | | | | | | | | | | |
| PCN01A | 2.00 | | | | | | | | | | |
| PCN02A | | 2.00 | | | | | | | | | |
| PCN03A | | | 2.00 | | | | | | | | |
| PCN04A | | | | 2.00 | | | | | | | |
| PCN05A | | | | | 2.00 | | | | | | |
| PNC06A | | | | | | 2.00 | | | | | |
| PCN07A | | | | | | | 2.00 | | | | |
| PCN08A | | | | | | | | 2.00 | | | |
| PCN09A | | | | | | | | | 2.00 | | |
| PCN10A | | | | | | | | | | 2.00 | |
| Thermolak™ 7525 | 3.50 | 3.50 | 3.50 | 3.50 | 3.50 | 3.50 | 3.50 | 3.50 | 3.50 | 3.50 | 5.50 |
| Thermolak™ 1010 | 1.00 | 1.00 | 1.00 | 1.00 | 1.00 | 1.00 | 1.00 | 1.00 | 1.00 | 1.00 | 1.00 |
| Basic violet 3 | 0.25 | 0.25 | 0.25 | 0.25 | 0.25 | 0.25 | 0.25 | 0.25 | 0.25 | 0.25 | 0.25 |
| Thermolak™ P1000S | 0.40 | 0.40 | 0.40 | 0.40 | 0.40 | 0.40 | 0.40 | 0.40 | 0.40 | 0.25 | 0.25 |
| Solvents | Weight (grams) | | | | | | | | | | |
| Dowanol PM | 80.0 | 80.0 | 80.0 | 80.0 | 80.0 | 80.0 | 80.0 | 80.0 | 80.0 | 80.0 | 80.0 |
| MEK | 15.0 | 15.0 | 15.0 | 15.0 | 15.0 | 15.0 | 15.0 | 15.0 | 15.0 | 15.0 | 15.0 |
| NMP | 5.00 | 5.00 | 5.00 | 5.00 | 5.00 | 5.00 | 5.00 | 5.00 | 5.00 | 5.00 | 5.00 |
| Laser Imaging | Energy Density (mJ/cm$^2$) | | | | | | | | | | |
| Clearing Point, CP | | | | | | | | | | | |
| 20 Sec. Dwell Time | 72 | 84 | 76 | 80 | 86 | 90 | 84 | 87 | 78 | 78 | 122 |
| 30 Sec. Dwell Time | 60 | 74 | 64 | 68 | 74 | 78 | 76 | 74 | 60 | 64 | 115 |

TABLE I-continued

|  | Ex. 11 | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|
| Correct Exposure, CE | | | | | | | | | | | |
| 20 Sec. Dwell Time | 120 | 132 | 120 | 126 | 130 | 132 | 130 | 132 | 124 | 124 | 165 |
| 30 Sec. Dwell Time | 106 | 118 | 110 | 120 | 122 | 118 | 124 | 126 | 118 | 120 | 150 |
| Development at 23° C. | Coating Development Loss, CDL (%) | | | | | | | | | | |
| 20 Seconds | 4.20 | 1.60 | 1.80 | 1.50 | 3.70 | 1.40 | 2.40 | 1.50 | 3.20 | 2.20 | 7.50 |
| 30 Seconds | 6.80 | 3.90 | 3.85 | 3.00 | 5.60 | 2.80 | 4.60 | 2.80 | 5.40 | 4.20 | 11.0 |
| | Alcohol Resistance, CR (%) | | | | | | | | | | |
| PG Aqueous Solution | 82 | 83 | 85 | 87 | 82 | 87 | 84 | 88 | 80 | 84 | 72 |
| PM Aqueous Solution | 71 | 74 | 75 | 76 | 72 | 77 | 71 | 78 | 72 | 74 | 53 |
| Stabilat-20 | 98 | 99 | 100 | 100 | 99 | 100 | 99 | 100 | 99 | 99 | 92 |

It can be seen from this table that the printing plates comprising the copolymers of the invention showed several advantages compared to the printing plate without any such copolymer (Example 21). They required less energy for laser imaging, they showed lower coating development loss. They also exhibited better chemical resistance against alcohol substituted fountain solution, such as Stabilat D2010 and water solution, containing 60% Dowanol PM and propylene glycol. In contrast, it was observed that the coating of printing plate of Example 21 was totally dissolved 8 hours after immersion in a water solution containing 50% Dowanol PM.

In addition, the printing plates comprising the copolymers of the invention produced more than 180,000 high quality copies on paper. In contrast, the plate of Example 21 produced around 110,000 high quality copies.

Finally, it was observed that the printing plates were stable during storage for at least 12 months under normal room conditions.

The above tests show that the copolymers for positive-working printing plates typically provide fast laser imaging speed, high-resolution images, wide processing latitude, stable storage life, good chemical resistance and long print run on press.

Although the present invention has been described hereinabove by way of specific embodiments thereof, it can be modified, without departing from the spirit and nature of the subject invention as defined in the appended claims.

REFERENCES

The present description refers to a number of documents, the content of which is herein incorporated by reference in their entirety.

| U.S. Pat. Nos.: |
|---|
| 5,397,690; |
| 6,124,425; |
| 6,132,929; |
| 6,177,182; |
| 6,326,122; |
| 6,355,396; |
| 6,410,203; |
| 6,884,568; |
| 7,060,415; |
| 7,060,416; |
| 7,258,961; |
| 7,371,504; and |
| 7,473,515. |
| U.S. Provisional Patent Application: |
| 61/255,918 |

The invention claimed is:

1. A copolymer having the general structure:

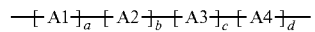

wherein:
   a, b, and d are molar ratios varying between about 0.01 and about 0.90 and c is a molar ratio varying between 0 and about 0.90,
   A1 represents monomer units of formula:

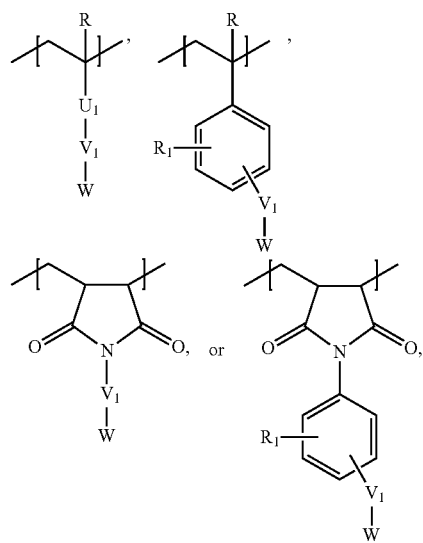

wherein:
   R is hydrogen, methyl or ethyl,
   $R_1$ is absent or represents one to four alkyl substituents; the alkyl substituents optionally comprising one or more ether, ester, amine, amide, urea, piperazinyl, sulfonamide, or carbamate functional groups, the alkyl substituents optionally being substituted with one or more cyano,
   $U_1$ is an amide or ester linker,
   $V_1$ is absent or represents alkyl optionally comprising one or more ether, ester, amine, amide, urea, piperazinyl, sulfonamide or carbamate functional group, the alkyl optionally being substituted with one or more cyano, and W is —CN or

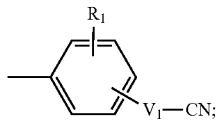

A2 represents monomer units of formula:

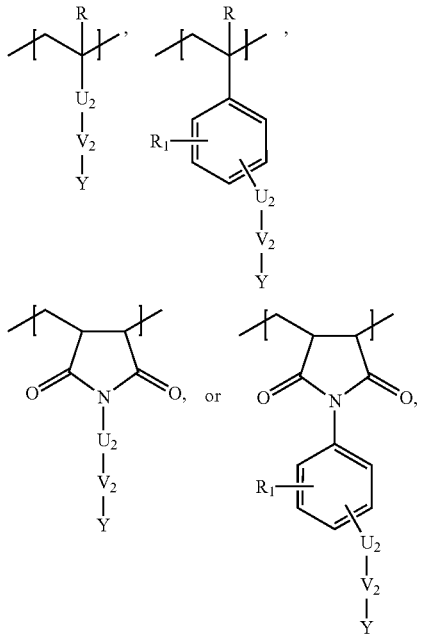

wherein:

R is hydrogen, methyl or ethyl, $R_1$ is absent or represents one to four alkyl substituents, the alkyl substituents optionally comprising one or more ether, ester, amine, amide, urea, piperazinyl, sulfonamide, or carbamate functional groups, $U_2$ is absent or represents an amide or ester linker, $V_2$ is absent or represents alkyl optionally comprising one or more ether, ester, amine, amide, urea, piperazinyl, sulfonamide or carbamate functional group, and Y is

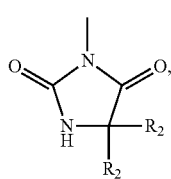

wherein $R_2$ each time it appears is independently hydrogen or alkyl optionally comprising one or more ether, ester, amine, amide, urea, piperazinyl, sulfonamide, or carbamate functional group;

A3 represents monomer units of formula:

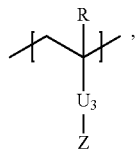

wherein

R is hydrogen, methyl or ethyl, $U_3$ is absent or is an amide or ester linker, and Z is alkyl or aryl, the alkyl being optionally substituted with one or more hydroxy, alkyloxy or halide and the aryl being optionally substituted with one or more alkyls that are optionally substituted with one or more hydroxy, alkyloxy or halide; and A4 represents monomer units of formula:

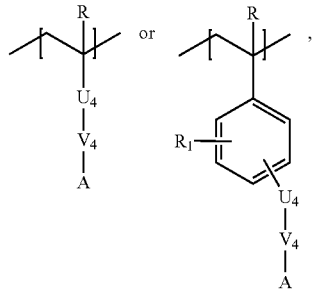

wherein R is hydrogen, methyl or ethyl, $R_1$ is absent or represents one to four alkyl substituents; the alkyl substituents optionally comprising one or more ether, ester, amine, amide, urea, piperazinyl, sulfonamide, or carbamate functional groups, $U_4$ is absent or represents an amide or ester linker, $V_4$ is absent or represents alkyl optionally comprising one or more ether, ester, amine, amide, urea, piperazinyl, sulfonamide or carbamate functional group, and A is —COOH, —PO(OH)$_2$,

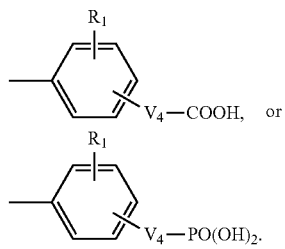

2. The copolymer of claim 1, wherein A1 is

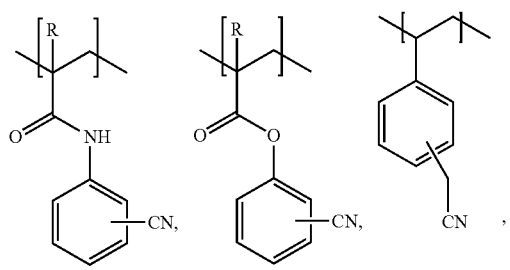

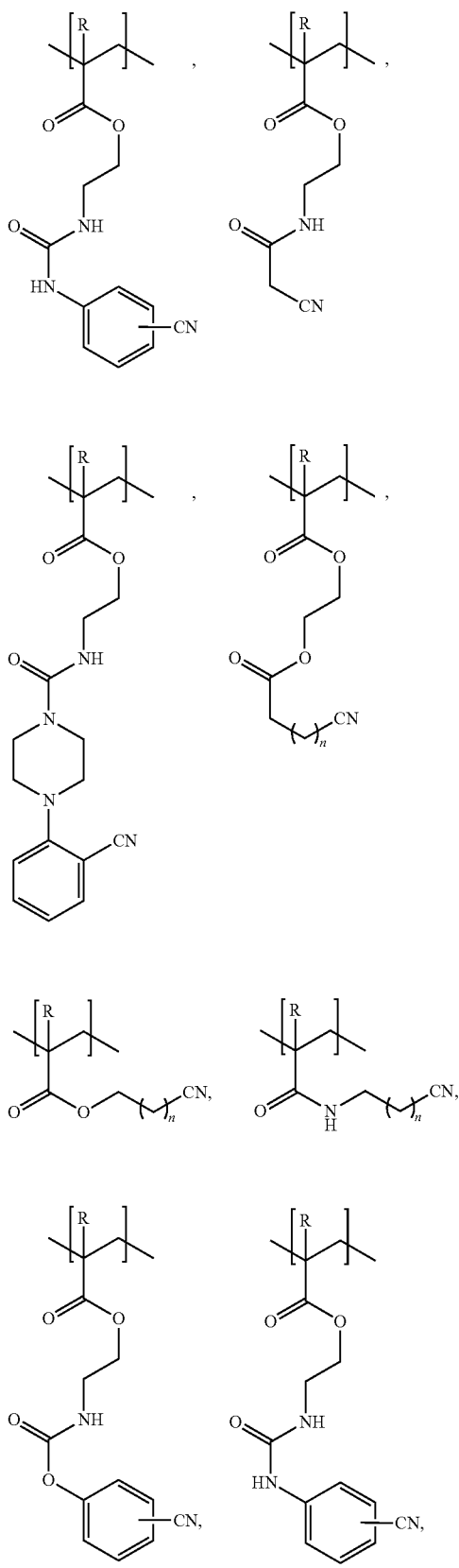
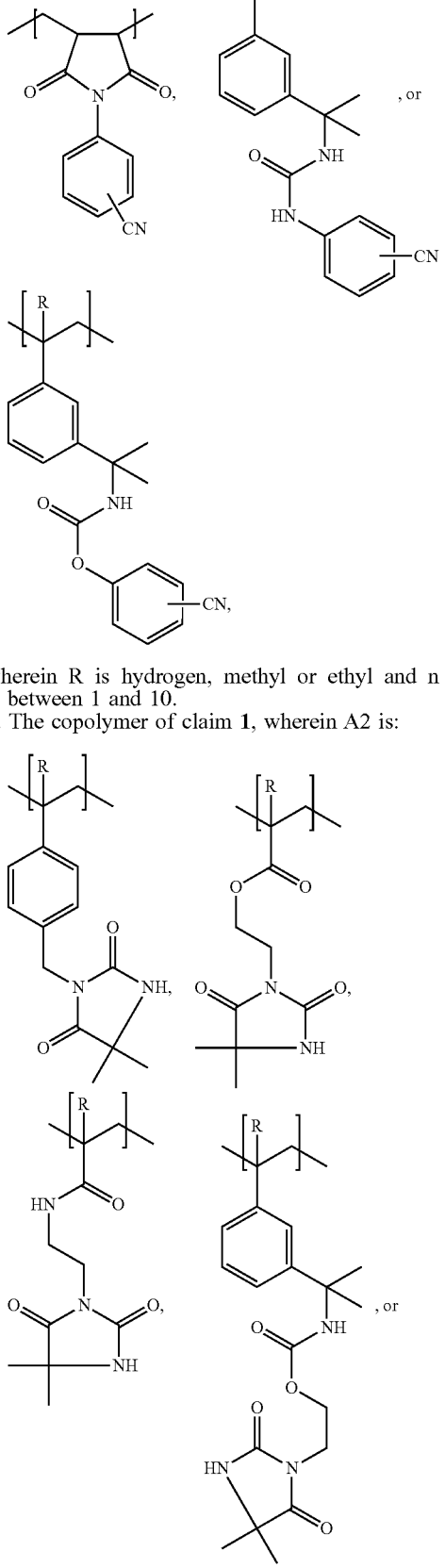
wherein R is hydrogen, methyl or ethyl and n varies between 1 and 10.
3. The copolymer of claim 1, wherein A2 is:

-continued

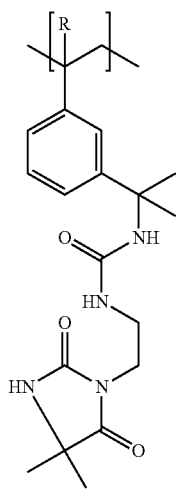

wherein R is hydrogen, methyl or ethyl.

4. The copolymer of claim 1, wherein c varies between about 0.01 and about 0.90.

5. The copolymer of claim 1, wherein A3 is:

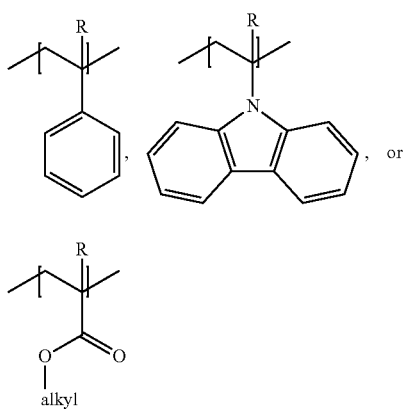

wherein R is hydrogen, methyl or ethyl.

6. The copolymer of claim 2, wherein A1 is:

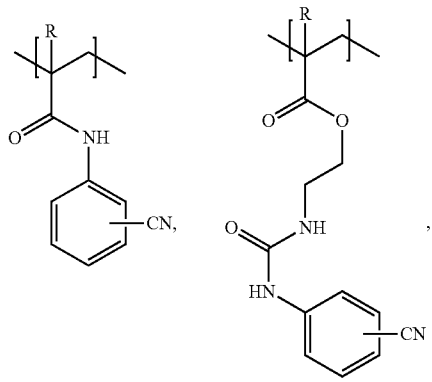

-continued

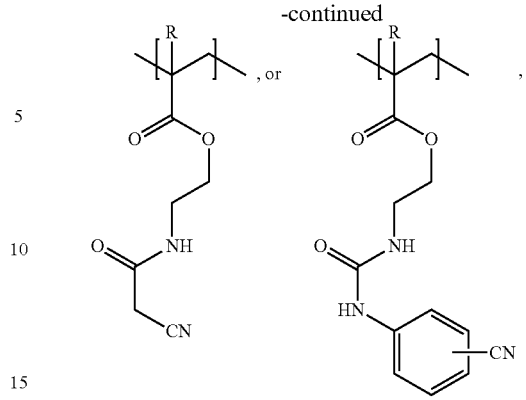

wherein R is hydrogen, methyl or ethyl.

7. The copolymer of claim 6, wherein R in A1 is methyl.

8. The copolymer of claim 3, wherein A2 is:

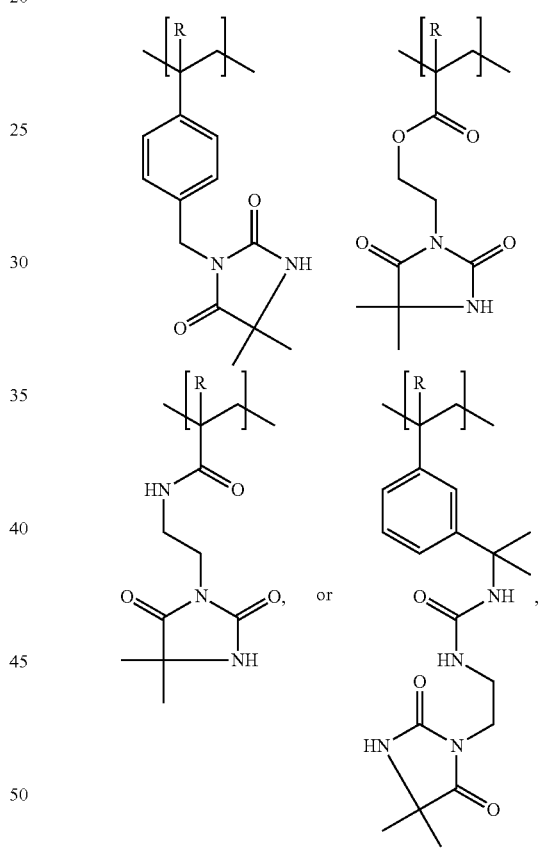

wherein R is hydrogen, methyl or ethyl.

9. The copolymer of claim 8, wherein R in A2 is methyl or ethyl.

10. The copolymer of claim 5, wherein A3 is of formula:

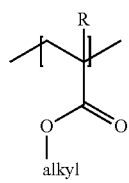

wherein R is hydrogen, methyl or ethyl.

11. The copolymer of claim 10, wherein the alkyl group in A3 is a methyl group.

12. The copolymer of claim 10, wherein the alkyl group in A3 is a methyl group and R in A3 is methyl.

13. The copolymer of claim 1, wherein A4 represents monomer units of formula:

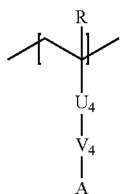

R, U$_4$, V$_4$, and A being as defined in claim 1.

14. The copolymer of claim 13, wherein A is —COOH.

15. The copolymer of claim 13, wherein in A4 R is methyl, U$_4$ is absent, V$_4$ is absent, and A is —COOH.

16. The copolymer of claim 1, being of formula:

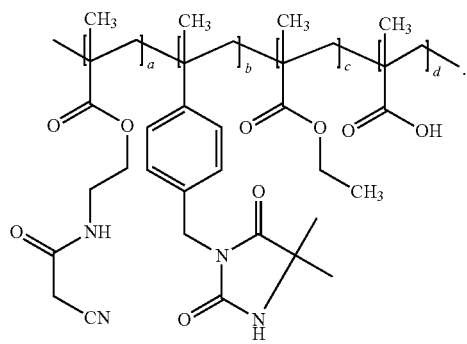

17. The copolymer of claim 1, being of formula:

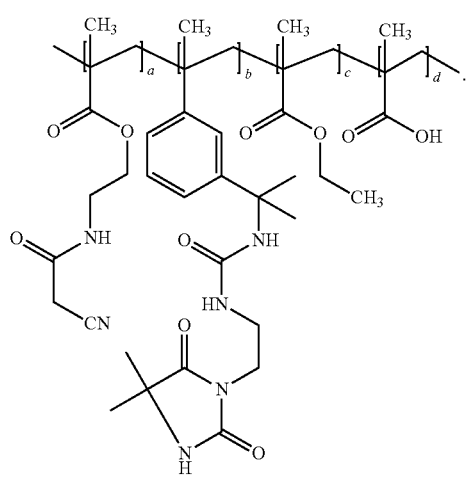

18. The copolymer of claim 1, being of formula:

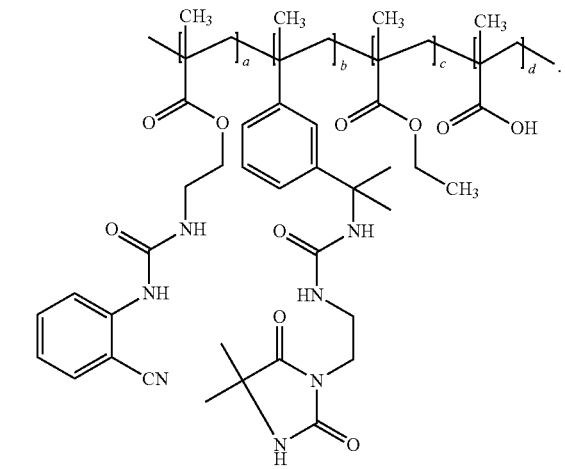

19. The copolymer of claim 1, being of formula:

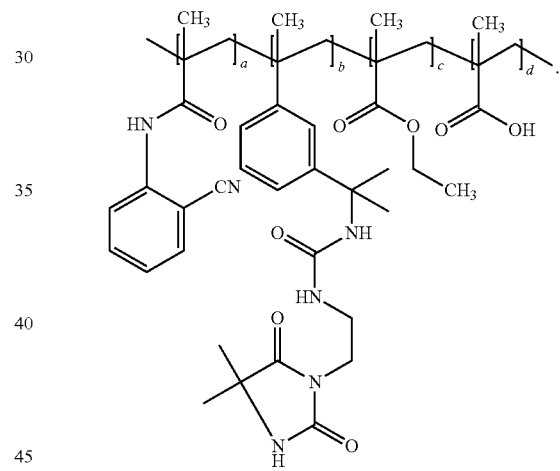

20. The copolymer of claim 1, being of formula:

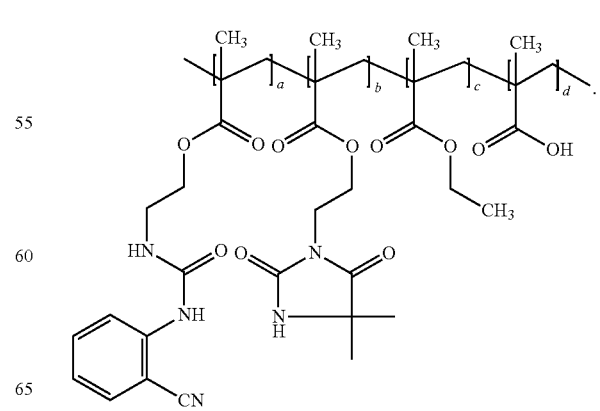

21. The copolymer of claim 1, being of formula:
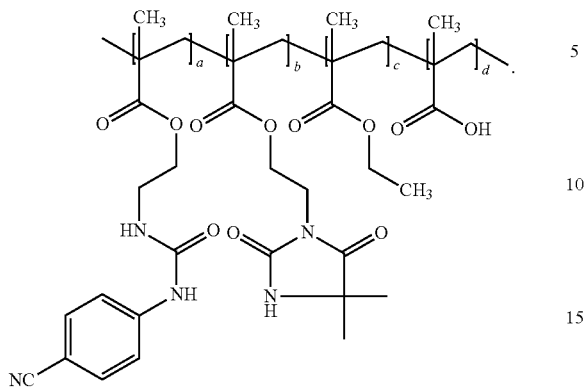
* * * * *